United States Patent
Wong et al.

(10) Patent No.: US 9,974,766 B2
(45) Date of Patent: May 22, 2018

(54) PRENYLATED ISOFLAVONES FOR TREATMENT OF SUBJECTS WITH MULTIDRUG-RESISTANT CANCER

(71) Applicant: Macau University of Science and Technology, Taipa, Macau (CN)

(72) Inventors: Kam Wai Wong, Taipa (CN); Yuen Kwan Law, Taipa (CN); Thomas Efferth, Mainz (DE); Onat Kadioglu, Taipa (CN); Liang Liu, Taipa (CN)

(73) Assignee: Macau University of Science and Technology, Taipa (MO)

( * ) Notice: Subject to any disclaimer, the term of this patent is extended or adjusted under 35 U.S.C. 154(b) by 0 days. days.

(21) Appl. No.: 14/953,860

(22) Filed: Nov. 30, 2015

(65) Prior Publication Data

US 2017/0151212 A1  Jun. 1, 2017

(30) Foreign Application Priority Data

Nov. 26, 2015 (AU) .............................. 2015101721

(51) Int. Cl.
 *A61K 31/352* (2006.01)
 *A61K 31/704* (2006.01)
 *A61K 31/337* (2006.01)

(52) U.S. Cl.
 CPC .......... *A61K 31/352* (2013.01); *A61K 31/337* (2013.01); *A61K 31/704* (2013.01)

(58) Field of Classification Search
 CPC ... A61K 31/352; A61K 31/704; A61K 31/337
 See application file for complete search history.

(56) References Cited

FOREIGN PATENT DOCUMENTS

WO    WO-0045165 A1 * 8/2000 ............. A61K 31/00

OTHER PUBLICATIONS

Vaclavikova et al., Bioorg. Med. Chem., 2006, 14, p. 4519-4525.*
Han, L., et al. Non-alkaloids extract from Stemona sessilifolia enhances the activity of chemotherapeutic agents through P-glycoprotein-mediated multidrug-resistant cancer cells. Nat Prod Res, 1-4 (2015).
Callaghan, R., Luk, F. & Bebawy, M. Inhibition of the multidrug resistance P-glycoprotein: time for a change of strategy? Drug Metab Dispos 42, 623-631 (2014).
Aller, S.G., et al. Structure of P-glycoprotein reveals a molecular basis for poly-specific drug binding. Science 323, 1718-1722 (2009).
Kim, T.H., et al. Resveratrol enhances chemosensitivity of doxorubicin in multidrug-resistant human breast cancer cells via increased cellular influx of doxorubicin. Biochim Biophys Acta 1840, 615-625 (2014).
Xu, L. et al. Enhanced activity of doxorubicin in drug resistant A549 tumor cells by encapsulation of P-glycoprotein inhibitor in PLGA-based nanovectors. Oncol Lett 7, 387-392 (2014).
Xing, Y., Wang, Z.H., Ma, D.H. & Han, Y. FTY720 enhances chemosensitivity of colon cancer cells to doxorubicin and etoposide via the modulation of P-glycoprotein and multidrug resistance protein 1. J Dig Dis 15, 246-259 (2014).
Gruber, J.V., Holtz, R., Sikkink, S.K. & Tobin, D.J. In vitro and ex vivo examination of topical Pomiferin treatments. Fitoterapia 94, 164-171.
Vesela, D., Kubinova, R., Muselik, J., Zemlicka, M. & Suchy, V. Antioxidative and EROD activities of osajin and pomiferin. Fitoterapia 75, 209-211 (2004).
Svasti, J., et al. Proteomic profiling of cholangiocarcinoma cell line treated with pomiferin from Derris malaccensis. Proteomics 5, 4504-4509 (2005).
Son, I.H., Chung, I.M., Lee, S.I., Yang, H.D. & Moon, H.I. Pomiferin, histone deacetylase inhibitor isolated from the fruits of Maclura pomifera. Bioorg Med Chem Lett 17, 4753-4755 (2007).
Yang, R., Hanwell, H., Zhang, J., Tsao, R. & Meckling, K.A. Antiproliferative activity of pomiferin in normal (MCF-10A) and transformed (MCF-7) breast epithelial cells. J Agric Food Chem 59, 13328-13336 (2011).
Bartosikova, L., et al. [Examination of the antioxidative and antidiabetic effect of pomiferin in alloxan-induced diabetes mellitus in an experiment (a pilot study)]. Ceska Slov Farm 56, 135-140 (2007).
Tajima, Y., et al. Nitensidine A, a guanidine alkaloid from Pterogyne nitens, is a novel substrate for human ABC transporter ABCB1. Phytomedicine : international journal of phytotherapy and phytopharmacology 21, 323-332 (2014).
Morris, G.M., et al. AutoDock4 and AutoDockTools4: Automated Docking with Selective Receptor Flexibility. J Comput Chem 30, 2785-2791 (2009).

* cited by examiner

*Primary Examiner* — Jonathan S Lau
(74) *Attorney, Agent, or Firm* — Renner Kenner Greive Bobak Taylor & Weber

(57) ABSTRACT

Prenylated isoflavones are suitable to specifically inhibit P-glycoprotein in multidrug-resistant cancer cells leading to an accumulation of cytotoxic compounds or therapeutic compounds in the cells while having exceptionally increased cytotoxic activity specifically towards multidrug-resistant cancer cells and while allowing for an increased activity of chemotherapeutic compounds towards which the cells are resistant.
Also in accordance with the present invention is a method for specifically targeting cancer cells with multidrug-resistance as well as a method of potentiating the activity of a chemotherapeutic compound in multidrug-resistant cancer cells. In a further aspect, a kit including a prenylated isoflavone and a chemotherapeutic compound is provided.

17 Claims, 27 Drawing Sheets

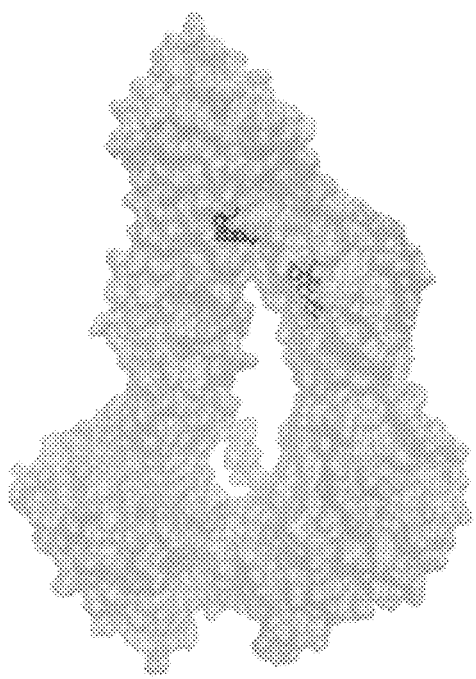
Fig. 2A
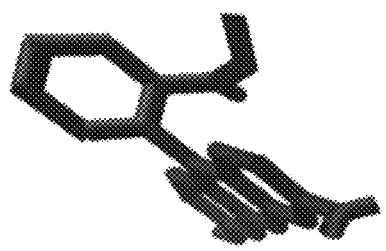
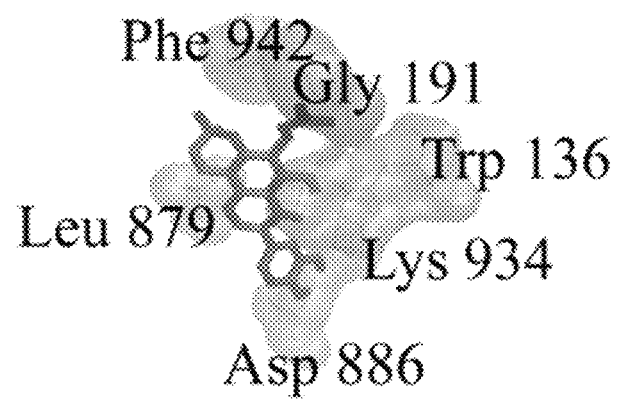
Fig. 2B
Fig. 2C

Fig. 3A
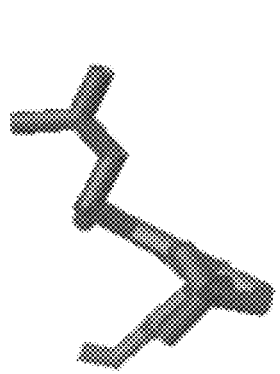
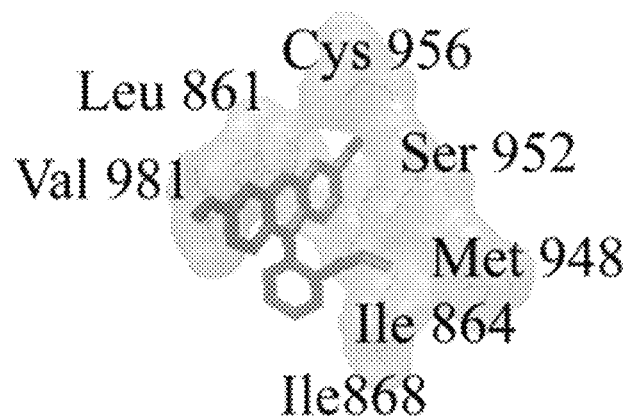
Fig. 3B                    Fig. 3C

PRENYLATED ISOFLAVONES FOR TREATMENT OF SUBJECTS WITH MULTIDRUG-RESISTANT CANCER

TECHNICAL FIELD

The present invention relates to the administration of a prenylated isoflavone and its effects on subjects with multidrug-resistant cancer, i.e. a specific subgroup of subjects with cancer. More specifically, the present invention is directed to a method for administering a prenylated isoflavone for treating a subject suffering from a multidrug-resistant cancer. Also in accordance with the present invention is a method for specifically targeting cancer cells with multidrug-resistance comprising contacting said cancer cells with the prenylated isoflavone as well as a method of potentiating the activity of a chemotherapeutic compound in multidrug-resistant cancer cells comprising contacting said cancer cells with the prenylated isoflavone. In a further aspect, the present invention provides a kit comprising the prenylated isoflavone and a chemotherapeutic compound.

BACKGROUND OF THE INVENTION

Drug-resistance in cancer is the major impediment to a successful treatment and the most difficult problem that needs to be overcome in order to ensure successful treatment of cancer. Multidrug-resistance (MDR) in cancer cells is generally a phenotype whereby cells display a reduced sensitivity to chemotherapeutic compounds based on several mechanisms, in particular due to an increase in drug efflux as most relevant form of MDR (Han, L. et al., Nat Prod Res, 2015, 1-4). Said multidrug-resistance can be a pre-existing one and, thus, evident at the onset of therapy (intrinsic) or alternatively be acquired after onset of therapy.

Members of the family of membrane proteins named ATP binding cassette (ABC transporter proteins) transporters or pumps usually consist of four domains which include two trans-membrane domains (TMDs) and two nucleotide binding domains (NBDs) as minimum functional unit to transport a substrate such as a chemotherapeutic compound triggered by ATP binding and respective hydrolysis. Members of said family are notorious mediators of MDR, actively effluxing a wide range of therapeutic compounds such as chemotherapeutic compounds irrespective of their concentration gradient. This significantly lowers their intracellular concentrations and, thus, their therapeutic effects in those cells. A prominent ABC transporter protein subfamily reported to modulate anticancer drug uptake is the "B" subfamily in particular with P-glycoprotein (P-gp, MDR1, or ABCB1) or ABCB5 including respective isoforms. Besides, common ABC transporters include the "C" subfamily such as with multidrug-resistance protein (MRP1 or ABCC1) and the "G"-subfamily such as with breast cancer resistance protein (ABCG2 or MXR).

ABC transporter proteins have been found to be constitutively expressed and overexpressed, respectively, in many multidrug-resistant cancers, wherein P-glycoprotein is considered for being a key player in the multidrug-resistant phenotype in cancer. Thereby, the expression of P-glycoprotein in multidrug-resistant cancer cells seems to be regulated by a wide range of factors including hypoxia, metabolic acidosis, generation of reactive oxygen species, namely P-glycoprotein is considered for being an important responder to chemical insult or environmental influences on cancer (Callaghan, R. et al., Drug Metab Dispos 2014, 42:623-31).

For example, expression and overexpression, respectively, of P-glycoprotein has been found in various types of cancers with resistance against commonly used and standard chemotherapeutic compounds such as anthracyclines, vinca alkaloids, topoisomerase-I and -II inhibitors, taxanes and the like, for example against doxorubicin or paclitaxel (taxol). Its broad specificity has been the subject of major attempts to inhibit said protein pump activity and to sensitize the potency of chemotherapeutic compounds (Callaghan, R. et al., Drug Metab Dispos 2014, 42:623-31). Accordingly, a strategy is to identify small-molecules that either act as direct P-glycoprotein inhibitors or compete with chemotherapeutic compounds for transport. Furthermore, the resolved structure of P-glycoprotein further revealed a molecular basis for poly-specific drug binding crucial for the lead optimization of chemotherapeutic compounds and MDR modulators (Aller, S. G. et al., Science, 2009, 323: 1718-22).

MDR modulators developed so far, however, fail to provide sufficient inhibition of ABC transporter proteins such as P-glycoprotein and/or did not demonstrate sufficient clinical utility in overcoming multidrug-resistance. Besides, most of the ABC transport protein inhibitors described so far have been initially developed for the treatment of other diseases than cancer like verapamil and these main drug activities may, thus, appear as non-tolerable side effects in cancer therapy. Unfortunately, progress in this area has been rather slow although having effective treatment options for multidrug-resistant cancer gets more and more important today.

Consequently, there is a strong need for methods and means allowing for an effective therapeutic treatment especially of multidrug-resistant cancer and cancer cells with a multidrug-resistant phenotype, respectively. In particular, efficacious treatment options are urgently required for specifically treating subjects with multidrug-resistant cancer with expression or overexpression of ABC transporter proteins, especially of P-glycoprotein, i.e. for treating said specific subgroup of subjects amongst subjects with cancer.

SUMMARY OF THE INVENTION

The present invention relates in a first aspect to a method for treating a subject suffering from a multidrug-resistant cancer, i.e. a cancer with multidrug-resistant phenotype, especially ABC-protein-dependent, in particular P-glycoprotein-dependent cancer. Said method for treating the subject with multidrug-resistant cancer comprises the step of administering an effective amount of a prenylated isoflavone or a pharmaceutically tolerable salt, solvate or anhydrate thereof to said subject, including any stereoisomers, diastereomers, enantiomers and racemates thereof.

Said prenylated isoflavone is derived from a specific subclass of flavonoids, namely the isoflavone-type flavonoids and more specifically the genistein-isoflavone-type. I.e. the prenylated isoflavone of the present invention is based on the general structure of Formula (I), referred to as "general isoflavone-type structure":

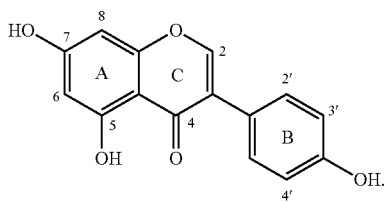

Formula (I)

The prenylated isoflavone of the present invention differs from said general structure of Formula (I) in that:
(i) it has at least one additional terpene moiety, namely at least one prenyl-group, i.e. at least one 3-methyl-but-2-en-1-yl-group, attached to a carbon atom in ring A of the general structure of Formula (I); and
(ii) it is optionally further modified by at least one of hydroxylation, alkylation such as methylation, esterification such as acetylation, glycosylation such as glucosylation, glucuronidation or hydrogenation.

In particular, the prenylated isoflavone of the present invention has a structure of Formula (II):

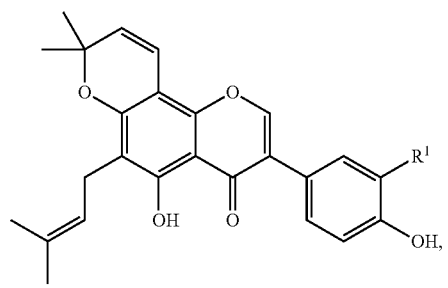

Formula (II)

with $R^1$ being hydrogen or —OH. In one embodiment of the invention, $R^1$ is hydrogen (H). In another embodiment of the invention, $R^1$ is —OH (hydroxyl-group). $R^1$ is in particular —OH, i.e. the prenylated isoflavone of the present invention has a structure of Formula (III):

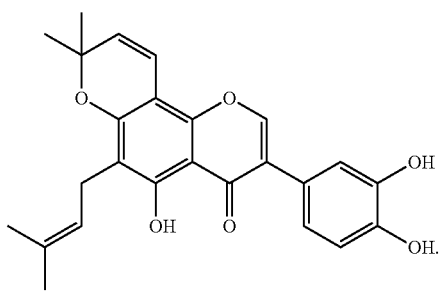

Formula (III)

The prenylated isoflavone of the present invention is, in particular, administered in combination with at least one chemotherapeutic compound commonly used for treating cancer, namely selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog.

According to the invention is also the prenylated isoflavone as described above for use as a medicament for the treatment of multidrug-resistant cancer, in particular P-glycoprotein-dependent cancer. Another aspect of the invention refers to the use of the prenylated isoflavone as described above for preparing a medicament for treatment of multidrug-resistant cancer, in particular P-glycoprotein-dependent cancer. The prenylated isoflavone as described above is in particular used in combination with chemotherapeutic compounds commonly used for treating cancer. The present invention also relates to the use of the prenylated isoflavone as described above as P-glycoprotein inhibitor for treating multidrug-resistant cancer.

In another aspect of the present invention, a method for specifically targeting cancer cells with multidrug-resistance is provided, in particular multidrug-resistant P-glycoprotein-dependent cancer cells. Said method comprises the step of contacting a population with multidrug-resistant cancer cells with the prenylated isoflavone as described above or a salt, solvate or anhydrate thereof. In particular, the growth of the multidrug-resistant cancer cells is suppressed and/or cell death is induced.

In still another aspect, the present invention provides a method of potentiating the activity of a chemotherapeutic compound in multidrug-resistant cancer cells. Said method comprises contacting said cancer cell with the prenylated isoflavone as described above, and with a chemotherapeutic compound commonly used for treating cancer, namely selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog, wherein said multidrug-resistant cancer cells are resistant against the chemotherapeutic compound.

Further in accordance with the present invention is a kit comprising an effective dose of the prenylated isoflavone as described above, and a chemotherapeutic compound commonly used for treating cancer, namely selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog. The kit may further comprise excipients, in particular pharmaceutically acceptable excipients, such as a carrier, salt, buffer, water, or a combination thereof.

Accordingly, the present invention provides a novel and highly advantageous option for treating a specific subgroup of subjects, namely subjects with multidrug-resistant cancers from various origins including either the administration of the aforementioned prenylated isoflavone alone or of said prenylated isoflavone as an adjuvant agent in combination with chemotherapeutic compounds commonly used for treating cancer, in particular those being substrates of at least one ABC-protein, in particular of P-glycoprotein. It has been found that the aforementioned prenylated isoflavone, in particular the prenylated isoflavone of Formula (II) or (III), are especially suitable to specifically inhibit P-glycoprotein activity in cancer cells leading to an accumulation of cytotoxic compounds or therapeutic compounds in said cells while having exceptionally increased cytotoxic activity specifically towards multidrug-resistant cancer cells such as various human cancer cells. Said prenylated isoflavone, in particular of Formula (II) or (III), hence, allows for effectively targeting multidrug-resistant cancer and cancer cells, respectively, either alone or in combination with conventional chemotherapeutic compounds as well as for potentiating the activity of commonly used chemotherapeutic compounds, and, thus, provides a highly advantageous treatment option to specifically address multidrug-resistant cancer and multidrug-resistant cancer cells, respectively.

In particular, the prenylated isoflavone of Formula (III) proved to specifically and advantageously target P-glycoprotein-dependent multidrug-resistant cancer cells through collateral sensitivity, i.e. it is especially suitable to selectively kill P-glycoprotein-dependent multidrug-resistant cancer cells, namely a significantly lower dose is required for treating the multidrug-resistant cancer cells compared to cancer cells of the same cell type without a multidrug-resistant phenotype, usually the $IC_{50}$ of the prenylated isoflavone towards multidrug-resistant cancer cells is significantly reduced.

BRIEF DESCRIPTION OF THE DRAWINGS

FIGS. 1A and 1B are 3D computational docking predicting with a docking calculation on the binding site and target region, respectively, of pomiferin (compound of Formula III) or Rhodamine (Rho123 or R123) on P-glycoprotein, wherein FIG. 1A shows the 3D structure and target region of pomiferin or Rho123, and FIG. 1B shows the 3D structure and selected residues of P-glycoprotein interacting with pomiferin.

FIGS. 2A, 2B and 2C are 3D computational docking predicting with a docking calculation on the binding site and target region, respectively, of pomiferin with pre-docked Rho123 on P-glycoprotein. FIG. 2A shows the 3D structure and target region of pomiferin with pre-docked Rho123. FIG. 2B shows the calculated 3D structure of Rho123 interacting with P-glycoprotein. FIG. 2C shows the 3D structure and selected residues of P-glycoprotein interacting with pomiferin with pre-docked Rho123.

FIGS. 3A, 3B, and 3C are 3D computational docking predicting with a docking calculation on the binding site and target region, respectively, of Rho123 with pre-docked pomiferin on P-glycoprotein. FIG. 3A shows the 3D structure and target region of Rho123 with pre-docked pomiferin. FIG. 3B shows the calculated 3D structure of pomiferin interacting with P-glycoprotein. FIG. 3C shows the 3D structure and selected residues of P-glycoprotein interacting with Rho123 with pre-docked pomiferin.

FIG. 4A shows the curve obtained with flow cytometry analysis of a Rho123 efflux assay in unstained MCF-7 taxol/doxorubicin sensitive breast cancer cells. FIG. 4B shows the curve obtained with flow cytometry analysis of a Rho123 efflux assay in MCF-7 taxol/doxorubicin sensitive breast cancer cells in the Rho123 control group. FIG. 4C shows the curve obtained with flow cytometry analysis of a Rho123 efflux assay in MCF-7 taxol/doxorubicin sensitive breast cancer cells treated with 10 µM verapamil. FIG. 4D shows the curve obtained with flow cytometry analysis of a Rho123 efflux assay in MCF-7 taxol/doxorubicin sensitive breast cancer cells treated with 5 µM pomiferin. FIG. 4E shows the curve obtained with flow cytometry analysis of a Rho123 efflux assay in MCF-7 taxol/doxorubicin sensitive breast cancer cells treated with 10 µM pomiferin. FIG. 4F shows the curve obtained with flow cytometry analysis of a Rho123 efflux assay in MCF-7 taxol/doxorubicin sensitive breast cancer cells treated with 15 µM pomiferin. FIG. 4G shows the curve obtained with flow cytometry analysis of a Rho123 efflux assay in MCF-7 taxol/doxorubicin sensitive breast cancer cells treated with 20 µM pomiferin.

FIG. 5A shows the curve obtained with flow cytometry analysis of a Rho123 efflux assay in unstained MCF-7 taxol-resistant breast cancer cells. FIG. 5B shows the curve obtained with flow cytometry analysis of a Rho123 efflux assay in MCF-7 taxol-resistant breast cancer cells in the Rho123 control group. FIG. 5C shows the curve obtained with flow cytometry analysis of a Rho123 efflux assay in MCF-7 taxol-resistant breast cancer cells treated with 10 µM verapamil. FIG. 5D shows the curve obtained with flow cytometry analysis of a Rho123 efflux assay in MCF-7 taxol-resistant breast cancer cells treated with 5 µM pomiferin. FIG. 5E shows the curve obtained with flow cytometry analysis of a Rho123 efflux assay in MCF-7 taxol-resistant breast cancer cells treated with 10 µM pomiferin. FIG. 5F shows the curve obtained with flow cytometry analysis of a Rho123 efflux assay in MCF-7 taxol-resistant breast cancer cells treated with 15 µM pomiferin. FIG. 5G shows the curve obtained with flow cytometry analysis of a Rho123 efflux assay in MCF-7 taxol-resistant breast cancer cells treated with 20 µM pomiferin.

FIG. 6A shows the curve obtained with flow cytometry analysis of a Rho123 efflux assay in unstained MCF-7 doxorubicin-resistant breast cancer cells. FIG. 6B shows the curve obtained with flow cytometry analysis of a Rho123 efflux assay in MCF-7 doxorubicin-resistant breast cancer cells in the Rho123 control group. FIG. 6C shows the curve obtained with flow cytometry analysis of a Rho123 efflux assay in MCF-7 doxorubicin-resistant breast cancer cells treated with 10 µM verapamil. FIG. 6D shows the curve obtained with flow cytometry analysis of a Rho123 efflux assay in MCF-7 doxorubicin-resistant breast cancer cells treated with 5 µM pomiferin. FIG. 6E shows the curve obtained with flow cytometry analysis of a Rho123 efflux assay in MCF-7 doxorubicin-resistant breast cancer cells treated with 10 µM pomiferin. FIG. 6F shows the curve obtained with flow cytometry analysis of a Rho123 efflux assay in MCF-7 doxorubicin-resistant breast cancer cells treated with 15 µM pomiferin. FIG. 6G shows the curve obtained with flow cytometry analysis of a Rho123 efflux assay in MCF-7 doxorubicin-resistant breast cancer cells treated with 20 µM pomiferin.

FIG. 7A shows the curve obtained with flow cytometry analysis of a Rho123 efflux assay in unstained A549 taxol-resistant lung cancer cells. FIG. 7B shows the curve obtained with flow cytometry analysis of a Rho123 efflux assay in A549 taxol-resistant lung cancer cells in the Rho123 control group. FIG. 7C shows the curve obtained with flow cytometry analysis of a Rho123 efflux assay in A549 taxol-resistant lung cancer cells treated with 10 µM verapamil. FIG. 7D shows the curve obtained with flow cytometry analysis of a Rho123 efflux assay in A549 taxol-resistant lung cancer cells treated with 5 µM pomiferin. FIG. 7E shows the curve obtained with flow cytometry analysis of a Rho123 efflux assay in A549 taxol-resistant lung cancer cells treated with 10 µM pomiferin. FIG. 7F shows the curve obtained with flow cytometry analysis of a Rho123 efflux assay in A549 taxol-resistant lung cancer cells treated with 15 µM pomiferin. FIG. 7G shows the curve obtained with flow cytometry analysis of a Rho123 efflux assay in A549 taxol-resistant lung cancer cells treated with 20 µM pomiferin.

FIG. 8A shows the curve obtained with flow cytometry analysis of a Rho123 efflux assay in unstained HCT-8 taxol-resistant colon cancer cells. FIG. 8B shows the curve obtained with flow cytometry analysis of a Rho123 efflux assay in HCT-8 taxol-resistant colon cancer cells in the Rho123 control group. FIG. 8C shows the curve obtained with flow cytometry analysis of a Rho123 efflux assay in HCT-8 taxol-resistant colon cancer cells treated with 10 µM verapamil. FIG. 8D shows the curve obtained with flow cytometry analysis of a Rho123 efflux assay in HCT-8 taxol-resistant colon cancer cells treated with 5 µM pomiferin. FIG. 8E shows the curve obtained with flow cytometry analysis of a Rho123 efflux assay in HCT-8 taxol-resistant colon cancer cells treated with 10 µM pomiferin. FIG. 8F shows the curve obtained with flow cytometry analysis of a Rho123 efflux assay in HCT-8 taxol-resistant colon cancer cells treated with 15 µM pomiferin. FIG. 8G shows the curve obtained with flow cytometry analysis of a Rho123 efflux assay in HCT-8 taxol-resistant colon cancer cells treated with 20 µM pomiferin.

FIG. 9A shows the pattern obtained by flow cytometry analysis of cell death in A549 taxol-resistant lung cancer cells of the control group. FIG. 9B shows the pattern obtained by flow cytometry analysis of cell death in A549 taxol-resistant lung cancer cells treated with 1 µM pomiferin. FIG. 9C shows the pattern obtained by flow cytometry analysis of cell death in A549 taxol-resistant lung cancer cells treated with 2 µM pomiferin. FIG. 9D shows the pattern obtained by flow cytometry analysis of cell death in A549 taxol-resistant lung cancer cells treated with 5 µM pomiferin. FIG. 9E shows the pattern obtained by flow cytometry analysis of cell death in A549 taxol-resistant lung cancer cells treated with 10 µM pomiferin. FIG. 9F shows the pattern obtained by flow cytometry analysis of cell death in A549 taxol-resistant lung cancer cells treated with 40 µM taxol. FIG. 9G shows the pattern obtained by flow cytometry analysis of cell death in A549 taxol-resistant lung cancer cells treated with 40 µM taxol and 1 µM pomiferin. FIG. 9H shows the pattern obtained by flow cytometry analysis of cell death in A549 taxol-resistant lung cancer cells treated with 40 µM taxol and 2 µM pomiferin. FIG. 9I shows the pattern obtained by flow cytometry analysis of cell death in A549 taxol-resistant lung cancer cells treated with 40 µM taxol and 5 µM pomiferin. FIG. 9J shows the pattern obtained by flow cytometry of cell death in A549 taxol-resistant lung cancer cells treated with 40 µM taxol and 10 µM pomiferin.

FIG. 10A shows the pattern obtained by flow cytometry analysis of cell death in HCT-8 taxol-resistant colon cancer cells of the control group. FIG. 10B shows the pattern obtained by flow cytometry analysis of cell death in HCT-8 taxol-resistant colon cancer cells treated with 1 µM pomiferin. FIG. 10C shows the pattern obtained by flow cytometry analysis of cell death in HCT-8 taxol-resistant colon cancer cells treated with 2 µM pomiferin. FIG. 10D shows the pattern obtained by flow cytometry analysis of cell death in HCT-8 taxol-resistant colon cancer cells treated with 5 µM pomiferin. FIG. 10E shows the pattern obtained by flow cytometry analysis of cell death in HCT-8 taxol-resistant colon cancer cells treated with 10 µM pomiferin. FIG. 10F shows the pattern obtained by flow cytometry analysis of cell death in HCT-8 taxol-resistant colon cancer cells treated with 40 µM taxol. FIG. 10G shows the pattern obtained by flow cytometry analysis of cell death in HCT-8 taxol-resistant colon cancer cells treated with 40 µM taxol and 1 µM pomiferin. FIG. 10H shows the pattern obtained by flow cytometry analysis of cell death in HCT-8 taxol-resistant colon cancer cells treated with 40 µM taxol and 2 µM pomiferin. FIG. 10I shows the pattern obtained by flow cytometry analysis of cell death in HCT-8 taxol-resistant colon cancer cells treated with 40 µM taxol and 5 µM pomiferin. FIG. 10J shows the pattern obtained by flow cytometry analysis of cell death in HCT-8 taxol-resistant colon cancer cells treated with 40 µM taxol and 10 µM pomiferin.

FIG. 11A shows the curve obtained with flow cytometry analysis of a Rho123 efflux assay in A549 taxol-resistant lung cancer cells in the Rho123 control group. FIG. 11B shows the curve obtained with flow cytometry analysis of a Rho123 efflux assay in A549 taxol-resistant lung cancer cells treated with 10 µM verapamil. FIG. 11C shows the curve obtained with flow cytometry analysis of a Rho123 efflux assay in A549 taxol-resistant lung cancer cells treated with 10 µM pomiferin. FIG. 11D shows the curve obtained with flow cytometry analysis of a Rho123 efflux assay in A549 taxol-resistant lung cancer cells treated with 10 µM pomiferin 3',4'-dimethyl ether. FIG. 11E shows the curve obtained with flow cytometry analysis of a Rho123 efflux assay in A549 taxol-resistant lung cancer cells treated with 10 µM pomiferin trimethyl ether. FIG. 11F shows the curve obtained with flow cytometry analysis of a Rho123 efflux assay in A549 taxol-resistant lung cancer cells treated with 10 µM isopomiferin. FIG. 11G shows the curve obtained with flow cytometry analysis of a Rho123 efflux assay in A549 taxol-resistant lung cancer cells treated with 10 µM osajin. FIG. 11H shows the curve obtained with flow cytometry analysis of a Rho123 efflux assay in A549 taxol-resistant lung cancer cells treated with 10 µM osajin 4'-methyl ether. FIG. 11I shows the curve obtained with flow cytometry analysis of a Rho123 efflux assay in A549 taxol-resistant lung cancer cells treated with 10 µM isoosajin.

DESCRIPTION OF THE EMBODIMENTS

Figure 1A:
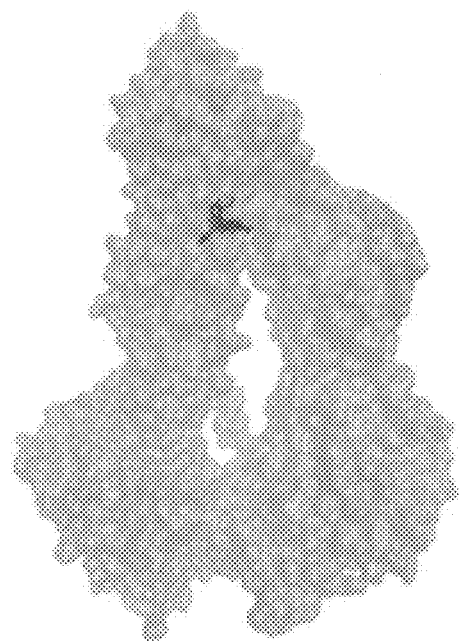

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

The present invention relates in a first aspect to a method for treating a subject suffering from a multidrug-resistant cancer, i.e. a cancer with multidrug-resistant phenotype. Said method of treating the subject with multidrug-resistant cancer comprises the step of administering an effective amount of a prenylated isoflavone or a pharmaceutically tolerable salt, solvate or anhydrate thereof to said subject. The prenylated isoflavone can be a synthetic one or obtained from extracts of respective plants, in particular a prenylated isoflavone obtained from *Maclura pomifera* (Osage Orange), in particular its fruits, or a respective synthetic prenylated isoflavone.

The term isoflavone generally refers to a specific subclass of flavonoids also known as isoflavone-type flavonoids. The prenylated isoflavone of the present invention is derived from said specific subclass of flavonoids, namely isoflavone-type flavonoids and more specifically from the genistein-isoflavone-type. I.e. the prenylated isoflavone of the present invention is based on the general structure of Formula (I) (also referred to as "general isoflavone-type-structure"):

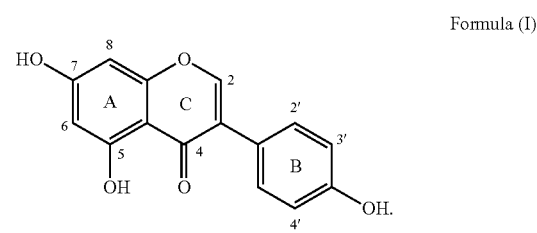

Formula (I)

More specifically, the term "prenylated isoflavone" as used in the present invention refers to a compound being derived from said general isoflavone-type-structure, i.e. from the structure of Formula (I), namely it is based on the general structure of Formula (I) and differs from said general isoflavone-type-structure in that:

(i) it contains at least one additional terpene moiety, namely at least one prenyl-group attached to a carbon atom in ring A of the general isoflavone-type-structure; and (ii) it is optionally further modified by at least one of hydroxylation, alkylation such as methylation, esterification such as acetylation, glycosylation such as glucosylation, glucuronidation or hydrogenation.

A "prenyl-group" is a 3-methyl-but-2-en-1-yl-group. Preferably, the prenylated isoflavone of the present invention comprises at least one prenyl-group in 6-position in ring A of the general isoflavone-type-structure, i.e. attached to the $C_6$ atom in the A ring or in 8-position in ring A of the general isoflavone-type-structure, i.e. attached to the $C_8$ atom in the A ring.

Preferably, the prenylated isoflavone of the present invention comprises at least two prenyl-groups, namely
at least a first prenyl-group attached to the $C_6$ atom in ring A of the general isoflavone-type-structure; and
a second prenyl-group attached to the $C_8$ atom in ring A of the general isoflavone-type-structure.

Preferably, the prenylated isoflavone of the present invention comprises at least two prenyl-groups, wherein one of the prenyl-groups forms a heterohydrocarbon ring structure with an OH-group in the general isoflavone-type-structure, i.e. cyclizes with the OH-group to form a 6-membered ring structure such as exemplified in Formulas (II), (III) and (X) given below. In further preferred embodiments of the present invention, the prenylated isoflavone comprises two prenyl-groups with a first prenyl-group attached to $C_6$ in the A-ring and the second prenyl-group attached to $C_8$ in the A-ring.

In a most preferred embodiment of the present invention, the prenyl-group attached to $C_8$ in ring A cyclizes with the OH-group attached to $C_7$ in ring A, such that a heterohydrocarbon ring is formed having the structure:

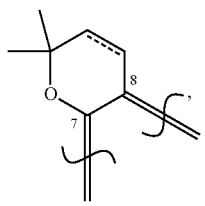

wherein ===== represents a single or double bond. In particular, the heterohydrocarbon ring has the following structure, i.e. ===== represents a double bond:

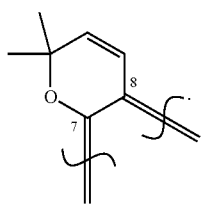

Optionally in said embodiment, a second prenyl-group at $C_6$ in ring A cyclizes with the OH-group at $C_5$ in ring A of the general isoflavone-type-structure to form a second 6-membered heterohydrocarbon ring, i.e. a ring having the structure

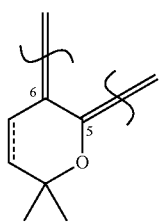

wherein ===== represents a single or double bond. In particular, the heterohydrocarbon ring has the following structure, i.e. ===== represents a single bond:

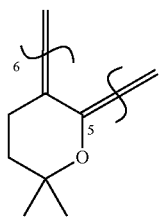

In such embodiments, two 6-membered heterohydrocarbon rings are present in the prenylated isoflavone of the present invention.

"Hydroxylation" refers to the presence of at least one additional OH-group in particular bonded to ring B in the general isoflavone-type-structure preferably one additional OH-group in 3' position in the B ring. "Alkylation" refers to the presence of at least one straight chain or branched $C_1$ to $C_3$ alkyl-group, i.e. an alkyl group having 1 to 3 carbon atoms, in particular of at least one methyl group such as one, two or three methyl groups preferably attached to oxygen atoms in OH-groups, in particular OH-groups in ring B and/or ring A, in the general isoflavone-type-structure or further present OH-groups, thus, forming alkoxy—such as methoxy-substituents. "Esterification" refers to the presence of at least one alkylester, i.e. a carboxylic acid has been attached to an OH-group in the isoflavone-type-structure or to a further present OH-group via an ester linkage. More specifically, esterification refers to the presence of an alkanoyl-group attached to an OH-group in the general isoflavone-type-structure or to a further present OH-group forming an alkanoyloxy-group. "Alkanoyl-group" is a carbonyl group bonded to an alkyl, which alkyl can be saturated or unsaturated, i.e. can contain at least one double or triple bond and usually has not more than 12 carbon atoms. Preferably, esterification refers to "acetylation", i.e. the presence of at least one acetyl-group attached to oxygen atoms in OH-groups, thus, forming acetoxy-groups. "Glycosylation" means presence of at least one carbohydrate-moiety in particular glucose-moiety (glucosylation) attached to an OH-group in the general isoflavone-type-structure or to a further present OH-group. Glucuronidation or glucuronosylation is the addition of at least one glucuronic acid-moiety to an OH-group in the general isoflavone-type-structure or to a further present OH-group. Hydrogenation refers to the presence of additional pairs of hydrogen atoms such as one additional pair of hydrogen atoms.

In embodiments of the present invention, the prenylated isoflavone is based on the general isoflavone-type-structure, wherein it differs from said structure in that:
(i) it contains a first prenyl-group present in 6-position in ring A, i.e. attached to the $C_6$ atom in the A ring and a second prenyl group attached to $C_8$ in the A ring, which second prenyl-group is cyclized with the OH-group at $C_7$ in the A ring; and wherein the first prenyl-group is optionally cyclized with the OH-group at $C_5$ in the A ring; and
(ii) it is optionally modified, further preferably it is modified, by at least one of
hydroxylation, in particular one additional OH-group in 3' position in the B ring is present;
methylation, in particular methyl groups are present attached to one or more of the OH-group in 4' position in the B ring, the OH-group at $C_5$ in the A ring or the additional OH-group in 3' position in the B ring; and/or
hydrogenation, in particular two additional hydrogen atoms are present.

In these embodiments of the present invention, the prenylated isoflavone can, in particular, be selected from one compound of Formula (III) to (IX) or a mixture thereof:

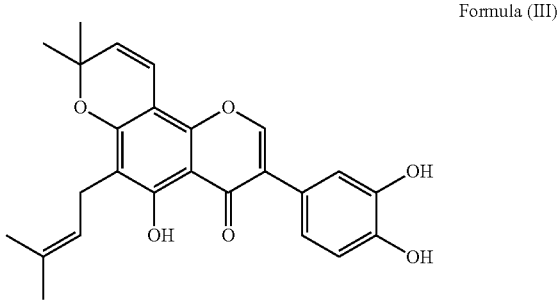

Formula (III)

(also known as pomiferin or (3-(3,4-dihydroxyphenyl)-5-hydroxy-8,8-dimethyl-6-(3-methylbut-2-enyl)pyrano[2,3-h] chromen-4-one);

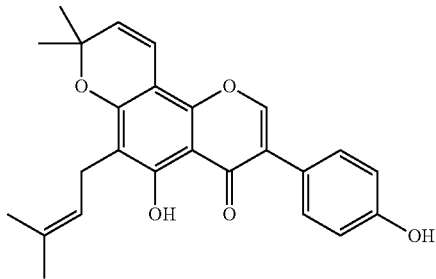

Formula (IV)

(also known as osajin or 5-hydroxy-3-(4-hydroxyphenyl)-8,8-dimethyl-6-(3-methylbut-2-enyl)pyrano[2,3-h] chromen-4-one);

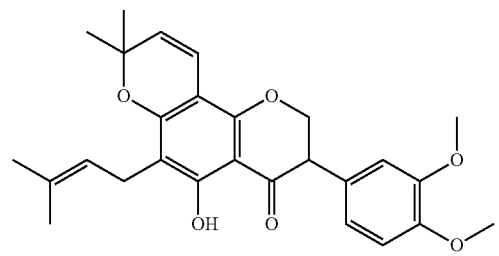

Formula (V)

(also known as pomiferin 3',4'-dimethyl ether);

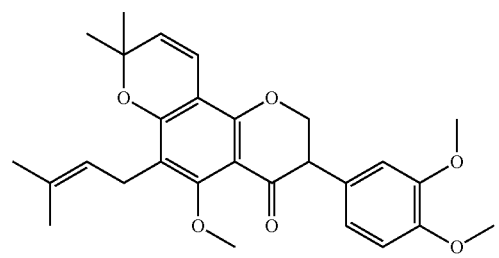

Formula (VI)

(also known as pomiferin trimethyl ether);

Formula (VII)

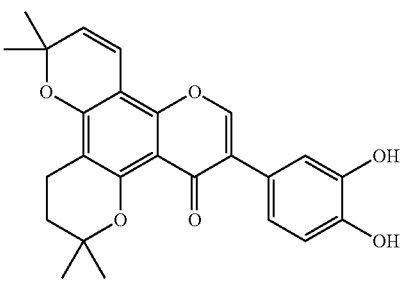

(also known as isopomiferin or 7,8-dihydro-3-(3,4-dihydroxyphenyl)-6,6,10,10-tetramethyl-4H,6H,10H-benzo[1,2-b:3,4-b':5,6-b"]tripyran-4-one);

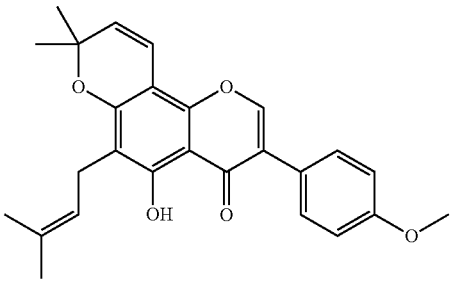

Formula (VIII)

(also known as osajin 4'-methyl ether); and/or

Formula (IX)

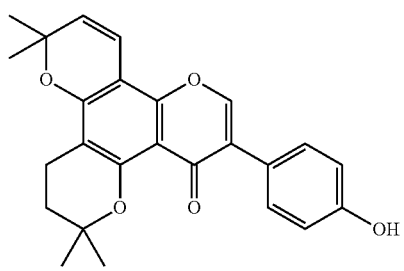

(also known as isoosajin or 3,4-dihydro-11-(4-hydroxyphenyl)-2,2,6,6-tetramethyl-2H,6H,12H-benzo[1,2-b:3,4-b':5,6-b"]tripyran-12-one).

In particular, the prenylated isoflavone in these embodiments of the present invention is selected from the compound of Formula (III), Formula (IV), Formula (VII), Formula (IX) or mixtures thereof, in particular selected from the compound of Formula (III), Formula (IV), Formula (VII) or Formula (IX).

In preferred embodiments of the present invention, the prenylated isoflavone of the present invention is based on the general isoflavone-type-structure, wherein it differs from said structure in that:

(i) it contains a first prenyl-group present in 6-position in ring A, i.e. attached to the $C_6$ atom in the A ring and a second prenyl group attached to $C_8$ in the A ring, which second prenyl-group is cyclized with the OH-group at $C_7$ in the A ring; and (ii) it is optionally modified, further preferably it is modified, by hydroxylation, in particular one additional OH-group in 3' position in the B ring is present.

Also contemplated by the present invention are any pharmaceutically acceptable salts, hydrates, solvates, anhydrates as well as enantiomers and their mixtures, stereoisomeric forms, racemates, diastereomers and their mixtures of the prenylated isoflavone of the present invention.

As used herein, the term "solvate" refers to a complex of variable stoichiometry formed by a solute, i.e. the prenylated isoflavone, and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition. The terms stereoisomers, diastereomers, enantiomers and racemates are known to the skilled person.

Preferably, the prenylated isoflavone of the present invention has a structure of Formula (II):

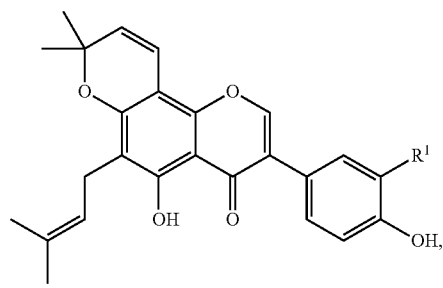

Formula (II)

with R¹ being hydrogen or —OH.

In one embodiment of the present invention, R¹ is hydrogen. In another embodiment of the present invention, R¹ is —OH.

Accordingly, in an embodiment of the present invention, the compound has a structure of Formula (IV):

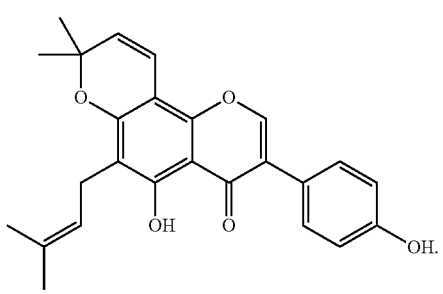

Formula (IV)

Said compound of Formula (IV) is also known as osajin (5-hydroxy-3-(4-hydroxyphenyl)-8,8-dimethyl-6-(3-methylbut-2-enyl)pyrano[2,3-h]chromen-4-one). Said compound can be prepared according to methods known to the skilled person or can be isolated from the fruits of *Maclura pomifera* (Osage Orange), which methods are known to the skilled person.

In a most preferred embodiment of the present invention, the prenylated isoflavone of the present invention has the structure of Formula (III):

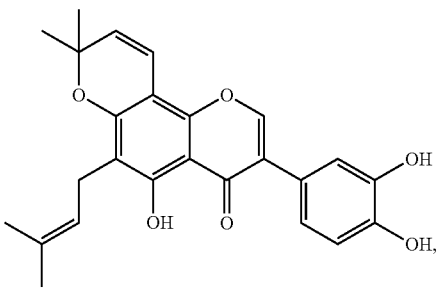

Formula (III)

including any salt, solvate or anhydrate thereof and including any stereoisomer, diastereomer, enantiomer or racemate thereof.

Said prenylated isoflavone of Formula (III) is also known as pomiferin (3-(3,4-dihydroxyphenyl)-5-hydroxy-8,8-dimethyl-6-(3-methylbut-2-enyl)pyrano[2,3-h] chromen-4-one) and can be prepared according to methods known to the skilled person or can be isolated from the fruits of *Maclura pomifera* (Osage Orange), which methods are known to the skilled person.

In still other embodiments of the present invention, the prenylated isoflavone has a structure of Formula (X):

Formula (X)

with R¹ being hydrogen or —OH. In one embodiment, R¹ is hydrogen, i.e. the compound is a compound of Formula (IX). In another embodiment, R¹ is —OH, i.e. the compound is a compound of Formula (VII).

The expression "effective amount" and "effective dose" generally denote an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells.

The effective amount of the prenylated isoflavone of the present invention may depend on the species, body weight, age and individual conditions of the subject and can be determined by standard procedures such as with cell cultures or experimental animals. A concentration of the prenylated isoflavone such as the prenylated isoflavone of Formula (II) or (X) or in particular of Formula (III) for treating the subject may, for example, be at least 1 µM, preferably at least 5 µM, in particular at least 10 µM. The prenylated isoflavone is preferably administered for at least 12 h, preferably at least 24 h, more preferably at least 48 h and in particular at least 72 h.

The subject can be a human or animal, in particular the subject is a human. The subject is, thus, preferably a human having a cancer with a multidrug-resistance.

The terms "cancer" and "cancerous" refer to or describe a physiological condition in subjects in which a population of cells are characterized by unregulated cell growth. The term "tumor" simply refers to a mass being of benign (generally harmless) or malignant (cancerous) growth.

The multidrug-resistant cancer can be a multidrug-resistant cancer of any origin, in particular human origin. In particular, the multidrug-resistant cancer is selected from the group consisting of multidrug-resistant:
lymphoma,
bladder cancer,
renal carcinoma,
pancreatic cancer,
ovarian cancer,
liver cancer,
myeloma,
sarcoma,
lymphocytic leukemia,
lung cancer,
breast cancer, and
colon cancer.

Preferably, the cancer is selected from multidrug-resistant:
lung cancer
breast cancer, or
colon cancer.

The provided method is used and particularly effective in treating subjects whose cancer has become "multidrug-resistant". The term "multidrug-resistance" is generally used for an acquired or natural, i.e. intrinsic, resistance of a cancer or more specifically of a cancer having cancer cells being simultaneously resistant to a range of chemotherapeutic compounds that usually differ structurally and functionally. Multidrug-resistant cancer with acquired drug resistance is characterized by a resumption of its growth and/or reappearance after having seemingly gone into remission, despite the administration of increased doses of a chemotherapeutic compound.

Cancers with cancer cells that have developed resistance to or are naturally resistant to two or more chemotherapeutic compounds are said to be "multidrug-resistant" in the present patent application such as to chemotherapeutic compounds selected from the group consisting of topoisomerase-II inhibitors, anthracyclines, coordination complexes of platinum, taxanes, protein kinase inhibitors, vinca alkaloids or derivatives thereof, topoisomerase-I inhibitors and nucleotide analogs or precursor analogs. Usually, a multidrug-resistant cancer is a cancer with cancer cells being resistant against three or more, five or more or even ten or more chemotherapeutic compounds such as those mentioned above. In preferred embodiments of the present invention, the multidrug-resistant cancer is a cancer having multidrug-resistant cancer cells, i.e. cancer cells which have developed resistance to or are naturally resistant to two or more chemotherapeutic compounds, wherein said multidrug-resistant cancer cells are resistant against at least one of paclitaxel (taxol), doxorubicin, cisplatin, etoposide and staurosporine, in particular against one of taxol or doxorubicin or both of them.

A cancer is multidrug-resistant if it comprises cancer cells which are multidrug-resistant, in particular if more than 30% of cancer cells, more preferably more than 50% of cancer cells in said cancer are multidrug-resistant. Accordingly, the cancer cells with multidrug-resistant phenotype will show less sensitive or more tolerant to most common chemotherapeutic agents. In practice, this can be determined by taking a sample of the cancer and determining the percentage of cancer cells with multidrug-resistance.

A multidrug-resistance can be detected in a subject, cancer, tissue, or cell by administering to the subject, tissue, or cell, compounds such as chemotherapeutic compounds and determining the activity of the chemotherapeutic compounds such as the induction of cell death or the inhibition of the proliferation of cancer cells compared to a reference control, namely cells or tissue of the same cell or tissue type, a cancer or a subject that do not have multidrug-resistance.

The multidrug-resistance according to the present invention is in particular mediated by ABC transporter proteins (hereinafter "ABC-proteins") such as by P-glycoprotein, i.e. is associated with an enhanced expression or enhanced functional activity of at least one ABC-protein in the multidrug-resistant cancer cells, in particular of P-glycoprotein. ABC-proteins are transporter proteins that may act to remove chemotherapeutic compounds from cells. The, thus, resulting multidrug-resistant phenotype can be specifically detected in a subject, tissue, cancer or cell by administering to the subject, tissue, or cell, a compound such as a chemotherapeutic compound which is transported by the ABC-proteins, i.e. is a substrate to ABC-proteins such as to P-glycoprotein. The method then encompasses determining the amount of said chemotherapeutic compound in the cells compared with the amount in a reference control, i.e. a subject, a tissue, cancer or a cell of the same cell or tissue type that do not express said multidrug-resistance phenotype, namely with ABC-protein expression as present in non-cancerous cells, in particular cancer cells or tissue without the multidrug-resistance phenotype or non-cancerous cells or tissue.

A multidrug-resistant cancer having cancer cells with an enhanced expression and/or enhanced functional activity of at least one ABC-protein is referenced herein as "ABC-protein-dependent cancer." Said ABC-protein is in particular selected from the "B" subfamily, "C" subfamily or "G" subfamily of ABC-proteins. Most preferably, said ABC-protein is P-glycoprotein, i.e. in most preferred embodiments of the present invention, the multidrug-resistant cancer is a P-glycoprotein-dependent multidrug-resistant cancer. Preferred "B" subfamily members include the protein encoded by ABCB1 (MDR1), ABCB4 (MDR2), ABCB5 or ABCB11 in humans or corresponding genes in other mammals. Preferred "C" subfamily members include the protein encoded by ABCC1 (MRP1) in humans or corresponding genes in other mammals. Preferred "G" subfamily members include the protein encoded by ABCG2 (BCRP) in humans or corresponding genes in other mammals. More preferably, the ABC-protein is of the "B" subfamily, in particular the ABC-protein is the protein encoded by ABCB1, ABCB4, ABCB5 or ABCB11 in humans or corresponding genes in other mammals which can transport drugs, in particular ABCB1 and/or ABCB5, most preferably ABCB1 or corresponding genes in other mammals, i.e. most preferably P-glycoprotein.

P-glycoprotein as used herein refers to the protein as encoded by the ABCB1 (MDR1) gene in humans or respective genes including SNPs and naturally occurring mutations to said gene and as encoded by corresponding genes in other mammals, respectively.

An enhanced expression and/or enhanced functional activity of at least one ABC-protein, i.e. ABC-protein-dependent multidrug-resistant cancer, means an expression and/or functional activity exceeding, in particular significantly exceeding, the one in normal cells or tissue, i.e. non-cancerous cells or tissue, or cancer cells without the multidrug-resistant phenotype. The term "enhanced expression" or "enhanced functional activity" of at least one ABC-protein such as P-glycoprotein includes embodiments in which the multidrug-resistant cancer cells express the ABC-protein such as P-glycoprotein, whereas in the reference control, i.e. cancer cells without the multidrug-resistant phenotype or non-cancerous cells of the same cell or tissue type, said ABC-protein such as P-glycoprotein is not expressed, at all. I.e. when said reference control does not express the ABC-protein such as P-glycoprotein, multidrug-resistant cancer cells having a detectable expression or functional activity of the ABC-protein such as P-glycoprotein are ABC-protein-dependent such as P-glycoprotein-dependent by definition.

In particular, the multidrug-resistant cancer is a cancer comprising multidrug-resistant P-glycoprotein-dependent cancer cells, i.e. multidrug-resistant cancer cells having an enhanced expression of P-glycoprotein and/or an enhanced functional activity of P-glycoprotein, in particular comprising more than 30% of said cancer cells, more preferably more than 50% of said cancer cells. The multidrug-resistant cancer is, thus, preferably a P-glycoprotein-dependent multidrug-resistant cancer.

Whether a multidrug-resistant cancer is an ABC-protein-dependent such as P-glycoprotein-dependent multidrug-resistant cancer can be determined by methods known to the skilled person in particular comprising immunological methods accompanied by the use of MDR-specific antibodies, immunocytochemistry and immunohistochemistry, respectively, by determining respective mRNA levels such as with Northern blots or quantitative RT-PCR, with MDR-specific antibodies in vivo or with an ABC-protein such as P-glycoprotein efflux assay detecting the efflux of a marker.

In particular, an ABC-protein such as P-glycoprotein efflux assay can be used for determining the activity of ABC-proteins, i.e. for determining whether multidrug-resistant cancer cells are ABC-protein-dependent. Markers which can be used in said efflux assay include drugs which are a substrate for the respective ABC-protein, a radionuclide or a dye like a fluorescent dye selected from Rhodamine123 (also referenced as "Rho123", 6-amino-9-(2-methoxycarbonylphenyl) xanthen-3-ylidene]azanium chloride), DiOC2 (3,3'-diethyloxacarbocyanine iodide) or Calcein AM (calcein o,o'-diacetate tetrakis(acetoxymethyl)ester). The cells to be analyzed are usually incubated with the marker at physiological conditions, i.e. in particular at about 37° C. for at least 20 min, in particular for at least 30 min and especially for about 1 h. Usually, the cells are washed subsequently at least 1-time, in particular more than 1-time preferably with a buffer, in particular 5-times with ice-cold Phosphate-buffered saline (PBS). Elimination from or, alternatively, retention of the marker in the multidrug-resistant cells can be determined and compared with a reference control, i.e. cells with ABC-protein expression as present in non-cancerous cells such as cancer cells that do not have a multidrug-resistance phenotype or non-cancerous cells of the same cell or tissue type. For example, fluorescence of a fluorescent marker can be determined by flow cytometry.

Preferably, an ABC-protein-dependent such as a P-glycoprotein-dependent multidrug-resistant cancer is a cancer comprising multidrug-resistant cancer cells with an expression of ABC-protein or ABC-protein functional activity exceeding the one in the reference control by at least 5%, in particular by at least 10%. For example, the expression or functional activity of P-glycoprotein in P-glycoprotein-dependent multidrug-resistant cancer cells is at least 5% or at least 10% higher than the expression or functional activity of P-glycoprotein in the reference control.

In particular embodiments of the present invention, an ABC-protein efflux assay is carried out to determine whether a multidrug-resistant cancer is ABC-protein-dependent. Thereby, the amount of marker, in particular a fluorescent dye, taken up by a multidrug-resistant cancer cell or a sample with such cancer cells is compared with the amount taken up by a reference control, namely cells with ABC-protein expression as present in non-cancerous cells, such as cancer cells that do not have a multidrug-resistance phenotype or non-cancerous cells of the same cell or tissue type. The multidrug-resistant cancer cells or the sample of multidrug-resistant cancer cells and, thus, the cancer is preferably considered for being ABC-protein-dependent according to the present invention, if the multidrug-resistant cancer cells have a reduced amount of marker such as dye, in particular an at least 20%, and more preferably at least 30% reduced amount of marker in the cells compared to the amount of marker in the reference control as revealed by the efflux assay or, alternatively, if the sample of multidrug-resistant cancer cells has a reduced percentage of cells with marker, namely an at least 20 percentage points and in particular at least 30 percentage points reduced percentage of cells with marker after carrying out the efflux assay compared to the reference control.

In particular, a sample of multidrug-resistant cancer cells and, thus, a cancer having those cells, is preferably considered for being P-glycoprotein-dependent, if it comprises less cells with marker such as dye like Rho123 as revealed by the P-glycoprotein efflux assay compared to the reference control which is a cell sample with P-glycoprotein expression as present in non-cancerous cells, in particular cancer cells that do not have a multidrug-resistance phenotype or non-cancerous cells of the same cell or tissue type. Namely, the percentage of cells with marker is preferably at least 20 percentage points, more preferably at least 30 percentage points and in particular at least 40 percentage points lower than the percentage of cells with marker in the reference control. More preferably, the percentage of cells with marker in P-glycoprotein-dependent multidrug-resistant cells is more than 50, and in particular at least 60 percentage points lower than the percentage of cells with marker in the reference control as revealed by the P-glycoprotein efflux assay.

The prenylated isoflavone in preferred embodiments of the present invention is administered in combination with an effective amount of at least one chemotherapeutic compound. As used herein, the term "chemotherapeutic compound" includes drugs which are advantageously and commonly administered to cancer or cancer cells without the multidrug resistance phenotype, i.e. which have been known to affect cancer cells.

In particular, the chemotherapeutic compound is a substrate for P-glycoprotein and selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog. Such chemotherapeutic compounds include etoposide, doxorubicin, daunorubicin, cisplatin, paclitaxel (taxol), docetaxel, staurosporine, vinblastine, vincristine, topotecan and methotrexate. Preferably, the chemotherapeutic compound is selected from the group consisting of cisplatin, doxorubicin, taxol, etoposide and staurosporine. Still more preferably, the chemotherapeutic compound is taxol, also named paclitaxel, or is doxorubicin. Further chemotherapeutic compounds which are substrates for the P-glycoprotein efflux can be used in combination with the prenylated isoflavone of the present invention, too.

In particular, the prenylated isoflavone of the present invention has a structure of Formula (II):

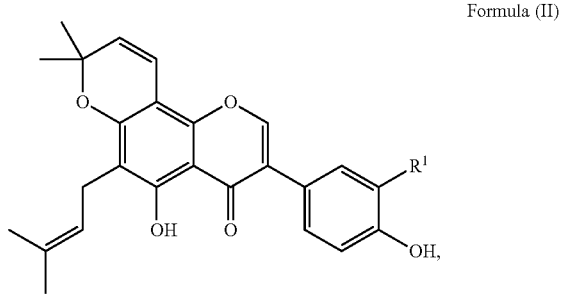

Formula (II)

with $R^1$ being hydrogen or —OH and the chemotherapeutic compound is selected from taxol or doxorubicin. In one embodiment of the present invention, $R^1$ is hydrogen. In another embodiment of the present invention, $R^1$ is —OH.

In especially preferred embodiments of the present invention, the prenylated isoflavone has the structure of Formula (III):

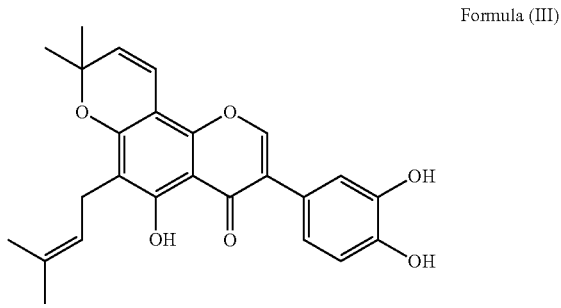 [SMILES: CC(C)=CCc1c2c(c3occ(-c4ccc(O)c(O)c4)c(=O)c3c1O)C=CC(C)(C)O2]

Formula (III)

and the chemotherapeutic compound is selected from taxol or doxorubicin, and is preferably taxol.

The chemotherapeutic compound can be administered before, after or simultaneously with the prenylated isoflavone, in particular before or simultaneously with the prenylated isoflavone.

The method of the present invention may comprise further steps before administering the prenylated isoflavone of the present invention, in particular the prenylated isoflavone of Formula (II), (X) or (III), of Obtaining a sample, in particular cancer cells, from the subject;

Testing said sample for the expression of at least one ABC-protein, in particular of P-glycoprotein, and/or the ABC-protein, in particular the P-glycoprotein, functional activity;

Optionally correlating the expression and/or functional activity of the at least one ABC-protein, in particular of P-glycoprotein, with an outcome and if conditions are met, administrating the prenylated isoflavone, in particular the prenylated isoflavone of Formula (II), (X) or (III), to said subject; alone or in combination with a chemotherapeutic compound, which is preferably a substrate for the ABC-protein, in particular for P-glycoprotein.

The skilled person is aware of methods for determining the expression of ABC-proteins, in particular P-glycoprotein, as described above including antibody assays or efflux assays for example by incubating the cells with a dye such as Rho123.

According to the invention is also the aforementioned prenylated isoflavone such as of Formula (II) or (X), in particular of Formula (III), for use as a medicament for the treatment of multidrug-resistant cancer, in particular P-glycoprotein-dependent multidrug-resistant cancer. Said prenylated isoflavone such as of Formula (II) or (X), in particular of Formula (III), can be used in an effective amount for treating an animal or a human, in particular a human. Another aspect of the invention refers to the use of the prenylated isoflavone described above, such as of Formula (II) or (X), in particular of Formula (III), for preparing a medicament for treatment of multidrug-resistant cancer, in particular P-glycoprotein-dependent multidrug-resistant cancer. The prenylated isoflavone, such as of Formula (II) or (X), in particular of Formula (III), may be used in combination with at least a further therapeutic compound, preferably a chemotherapeutic compound.

The present invention further provides a method for specifically targeting cancer cells with multidrug-resistance comprising the step of contacting a population of cancer cells with multidrug-resistance with a prenylated isoflavone as described above or a salt, solvate or anhydrate thereof. Preferably, the growth of the multidrug-resistant cancer cells is suppressed or cell death is induced, in particular cell death is induced. In particular, the prenylated isoflavone such as the prenylated isoflavone of Formula (II), (X) or (III) binds to and inhibits the P-glycoprotein activity in said multidrug-resistant cancer cells.

The inhibition of P-glycoprotein can be determined with a P-glycoprotein efflux assay by determining the amount of multidrug-resistant cancer cells in a sample with marker such as with Rho123 in the presence of the prenylated isoflavone of the present invention after carrying out the efflux assay compared to a reference control with multidrug-resistant cancer cells in the absence of the prenylated isoflavone. In particular, the percentage of cells with marker such as Rho123 is at least 20, more preferably at least 30 and in particular at least 40 percentage points increased compared to the reference control by the prenylated isoflavone of the present invention. Usually, the multidrug-resistant cancer cells are contacted with the prenylated isoflavone and incubated for at least 12 h, in particular for about 24 h at about 37° C. The reference control is, instead, not incubated with the prenylated isoflavone. Usually, the marker in particular Rho123 is subsequently added while further incubating at about 37° C. for at least 20 min, preferably for at least 30 min and in particular for about 1 h.

The multidrug-resistant cancer cells are in particular ABC-protein-dependent, most preferably P-glycoprotein-dependent. The multidrug-resistant cancer cells can be of any origin, in particular of human origin. In particular, the multidrug-resistant cancer cells are from a multidrug-resistant:

lymphoma,
bladder cancer,
renal carcinoma,
pancreatic cancer,
ovarian cancer,
liver cancer,
myeloma,
sarcoma,
lymphocytic leukemia, lung cancer,
breast cancer, or
colon cancer.

More preferably, the multidrug-resistant cancer cells are from multidrug-resistant:
lung cancer
breast cancer, or
colon cancer.

In preferred embodiments of the present invention, the multidrug-resistant cancer cells are resistant against at least one of paclitaxel (taxol), doxorubicin, cisplatin, etoposide and staurosporine, in particular against one of taxol or doxorubicin or both of them.

The concentration of the prenylated isoflavone used for contacting the multidrug-resistant cancer cells may range from 1 µM to 100 µM, preferably from 5 µM to 50 µM, in particular from 10 µM to 40 µM, more preferably between 5 µM and 30 µM, i.e. between 5 µmol/l (=5 mmol/m$^3$) and 30 µmol/l (=30 mmol/m$^3$), such as 15.2 µM to 27.1 µM. The multidrug-resistant cancer cells are preferably contacted with the prenylated isoflavone of the present invention for at least 12 h, preferably for at least 24 h, more preferably for at least 48 h and in particular for at least 72 h.

Preferably, the $IC_{50}$ of the prenylated isoflavone towards the multidrug-resistant cancer cells is at most 40 µM, more preferably at most 30 µM and in particular at most 20 µM after about 72 h. The Resistant Factor of the prenylated isoflavone of the present invention towards the multidrug-resistant cancer cells is preferably less than 0.98, more preferably less than 0.95 and in particular less than 0.8. The Resistant Factor is calculated by dividing the $IC_{50}$ of the prenylated isoflavone towards multidrug-resistant cells by its $IC_{50}$ towards cancer cells of the same cell type or tissue which do not have a multidrug-resistant phenotype. A Resistant Factor<1 indicates that a compound is especially effective in multidrug-resistant cancer cells compared to cancer cells of the same cell type or tissue which do not have a multidrug-resistant phenotype, i.e. is especially suitable to specifically target multidrug-resistant cancer cells.

The prenylated isoflavone of the present invention used for contacting the multidrug-resistant cancer cells may be, for example, selected from the compound of Formula (III), Formula (IV), Formula (VII), Formula (IX) or mixtures thereof, in particular selected from the compound of Formula (III), Formula (IV), Formula (VII) or Formula (IX).

Preferably, the prenylated isoflavone of the present invention used for contacting the multidrug-resistant cancer cells has a structure of Formula (II):

Formula (II)

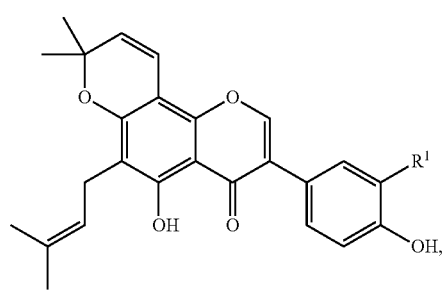

with R$^1$ being hydrogen or —OH. In one embodiment of the present invention, R$^1$ is hydrogen. In another embodiment of the present invention, R$^1$ is —OH.

In especially preferred embodiments of the present invention, the prenylated isoflavone used for contacting the multidrug-resistant cancer cells has the structure of Formula (III):

Formula (III)

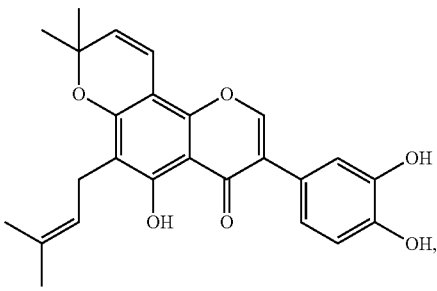

and the cancer cells are contacted with between 5 µM and 30 µM of said prenylated isoflavone.

The step of contacting the cells with the prenylated isoflavone of the present invention, such as the prenylated isoflavone of Formula (II), (X) or (III), may be carried out by applying an incubation solution comprising the prenylated isoflavone such as the prenylated isoflavone of Formula (II), (X) or in particular the prenylated isoflavone of Formula (III) to said cells, which incubation solution may further comprise suitable excipients such as solvents, buffers or a suitable growth medium. The method may further comprise contacting said cells with a further therapeutic compound, in particular a chemotherapeutic compound.

In particular embodiments, the present invention refers to a method for inhibiting the proliferation of cells or for inducing cell death, in particular for inducing cell death, comprising the step of contacting cancer cells that include multidrug-resistant cancer cells which are P-glycoprotein-dependent with an effective amount of the prenylated isoflavone described above, such as the compound of Formula (II) or (X) or in particular the prenylated isoflavone of Formula (III), or a salt, solvate or anhydrate thereof; and inhibiting the proliferation of the multidrug-resistant P-glycoprotein-dependent cancer cells or inducing cell death of those cells, wherein P-glycoprotein is inhibited and the proliferation of the multidrug-resistant P-glycoprotein-dependent cancer cells is selectively inhibited or cell death of those cells is selectively induced.

In a further aspect, the present invention refers to a method of potentiating the activity of a chemotherapeutic compound in multidrug-resistant cancer cells comprising contacting said cancer cells with
  a prenylated isoflavone as described above; and
  a chemotherapeutic compound, wherein the chemotherapeutic compound is selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog,
and wherein the multidrug-resistant cancer cells are resistant against the chemotherapeutic compound.

The prenylated isoflavone of the present invention is effective for potentiating the activity of the chemotherapeutic compound, i.e. for increasing the effectiveness of the chemotherapeutic compound to inhibit proliferation of the multidrug-resistant cancer cells, inducing cell death of the multidrug-resistant cancer cells, and/or indirectly inhibiting development of the multidrug-resistant cancer cells. In particular, the activity of the chemotherapeutic compound to inhibit proliferation or inducing cell death, i.e. apoptosis, is increased. "Potentiating the activity" as used herein means any measurable increase such as of at least 5%, preferably of at least 10% and more preferably of at least 20%. For example, potentiating the activity of a chemotherapeutic compound can be an increase with regard to cell death, in particular the percentage of total cell deaths after contacting the multidrug-resistant cancer cells with the chemotherapeutic compound and the prenylated isoflavone preferably for at least 12 h, in particular for about 24 h, is at least 5, more preferably at least 10 and in particular at least 20, and further preferably at least 25 and still more preferably at least 40 percentage points increased compared to the percentage of cell deaths in multidrug-resistant cancer cells which have been contacted with the chemotherapeutic compound, but not with the prenylated isoflavone.

The multidrug-resistant cancer cells are preferably contacted with from 1 μM to 100 μM of the prenylated isoflavone, preferably from 5 μM to 50 μM, in particular from 10 μM to 40 μM, more preferably between 4 μM and 20 μM, i.e. between 4 μmol/l (=4 mmol/m³) and 20 μmol/l (=20 mmol/m³). The cancer cells are preferably contacted with the prenylated isoflavone for at least 12 h, preferably for about 24 h. The step of contacting the cells with the prenylated isoflavone such as the prenylated isoflavone of Formula (II), (X) or (III) and the chemotherapeutic compound may be carried out by applying at least one incubation solution comprising the prenylated isoflavone and/or the chemotherapeutic compound to said cells which incubation solution may further comprise suitable excipients such as solvents, buffers or a suitable growth medium.

The multidrug-resistant cancer cells are contacted with the chemotherapeutic compound before, after or simultaneously with the prenylated isoflavone, in particular before or simultaneously with the prenylated isoflavone, more preferably simultaneously with the prenylated isoflavone. The chemotherapeutic compound is preferably selected from cisplatin, doxorubicin, paclitaxel (taxol), etoposide or staurosporine, in particular from taxol or doxorubicin.

The prenylated isoflavone of the present invention may be, for example, selected from the compound of Formula (III), Formula (IV), Formula (VII), Formula (IX) or mixtures thereof, in particular selected from the compound of Formula (III), Formula (IV), Formula (VII) or Formula (IX).

Preferably, the multidrug-resistant cancer cells are contacted with a prenylated isoflavone having a structure of Formula (II):

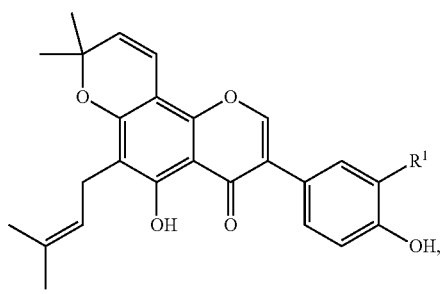

Formula (II)

with $R^1$ being hydrogen or —OH. In one embodiment of the present invention, $R^1$ is hydrogen. In another embodiment of the present invention, $R^1$ is —OH.

Most preferably, the multidrug-resistant cancer cells are contacted with a prenylated isoflavone having the structure of Formula (III):

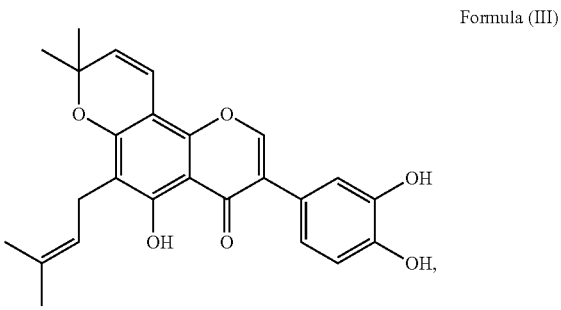 [SMILES: CC(C)=CCc1c2c(c3occ(-c4ccc(O)c(O)c4)c(=O)c3c1O)C=CC(C)(C)O2]

Formula (III)

wherein the multidrug-resistant cancer cells are preferably contacted with between 4 μM and 20 μM of the prenylated isoflavone of Formula (III).

The present invention further provides a kit comprising an effective dose of
  (i) a prenylated isoflavone as described above; and
  (ii) a chemotherapeutic compound selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog.

The kit may further comprise an instruction leaflet and/or means for determining ABC-protein, in particular P-glycoprotein, expression or functional activity. The kit may comprise excipients, in particular pharmaceutically acceptable excipients, such as a carrier, salt, buffer, water, or a combination thereof. The skilled person is able to select suitable excipients. Still further, the kit may comprise at least one container.

The prenylated isoflavone according to the invention can be present in solid, semisolid or liquid form to be administered by an oral, rectal, topical, parenteral or transdermal or inhalative route to a subject, preferably a human.

The chemotherapeutic compound in the kit may comprise one of cisplatin, doxorubicin, paclitaxel (taxol), etoposide and staurosporine, in particular one of taxol or doxorubicin.

The prenylated isoflavone in the kit of the present invention may be, for example, selected from the compound of Formula (III), Formula (IV), Formula (VII), Formula (IX) or mixtures thereof, in particular selected from the compound of Formula (III), Formula (IV), Formula (VII) or Formula (IX).

Preferably, the prenylated isoflavone in the kit has a structure of Formula (II):

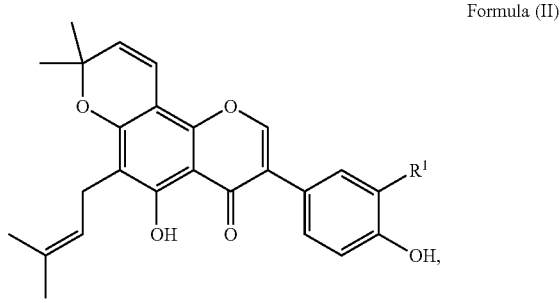

Formula (II)

with R¹ being hydrogen or —OH and the chemotherapeutic compound is taxol or doxorubicin. In one embodiment of the present invention, R¹ is hydrogen. In another embodiment of the present invention, R¹ is —OH.

In especially preferred embodiments, the prenylated isoflavone in the kit has the structure of Formula (III):

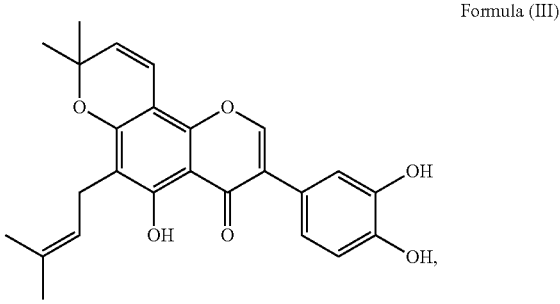 [SMILES: CC(C)=CCc1c2c(c3occ(-c4ccc(O)c(O)c4)c(=O)c3c1O)C=CC(C)(C)O2]

Formula (III)

and the chemotherapeutic compound is taxol or doxorubicin, more preferably taxol.

In still another aspect, the present invention concerns the use of the prenylated isoflavone, in particular the prenylated isoflavone of Formula (II), (X) or (III), or the kit described above for inhibiting P-glycoprotein in multidrug-resistant cancers and multidrug-resistant cancer cells, respectively, in particular for initiating cell death of multidrug-resistant cancer cells or for inducing collateral sensitivity in said multidrug-resistant cancer cells.

The inhibition of P-glycoprotein can be determined with a P-glycoprotein efflux assay by determining the amount of multidrug-resistant cancer cells in a sample with marker such as with Rho123 in the presence of the prenylated isoflavone of the present invention after carrying out the efflux assay compared to a reference control with multidrug-resistant cancer cells in the absence of the prenylated isoflavone. In particular, the percentage of cells with marker such as Rho123 is at least 20, more preferably at least 30 and in particular at least 40 percentage points increased compared to the reference control by the prenylated isoflavone of the present invention. Usually, the multidrug-resistant cancer cells are contacted with the prenylated isoflavone and incubated for at least 12 h, in particular for about 24 h at about 37° C. The reference control is, instead, not incubated with the prenylated isoflavone. Usually, the marker in particular Rho123 is subsequently added while further incubating at about 37° C. for at least 20 min, preferably for at least 30 min and in particular for about 1 h.

EXAMPLES

Multidrug-resistant MCF-7 breast (Kim, T. H. et al., Biochim Biophys Acta, 2014, 1840:615-25), A549 lung cancer (Xu, L. et al., Oncol Lett, 2014, 7:387-392), and HCT-8 colon cancer cells (Xing, Y. et al., J Dig Dis, 2014, 15:246-59) have been used for validation of the effects of the prenylated isoflavone of Formula (III), i.e. pomiferin, as overexpression of P-glycoprotein has been correlated with a multidrug-resistant phenotype which can be induced in these cells.

Example 1

Molecular Docking Studies

A previously generated homology model of human P-glycoprotein (Tajima, Y. et al. Phytomedicine: international journal of phytotherapy and phytopharmacology, 2014, 21:323-332) was used for molecular docking studies with AutoDock 4 (Morris, G. M. et al. J Comput Chem, 2009, 30:2785-2791) on the drug binding pocket.

The residues at the drug binding pocket of P-glycoprotein are: His61, Gly64, Leu65, Met69, Ser222, Leu304, Ile306, Tyr307, Phe336, Leu339, Ile340, Ala342, Phe343, Gln725, Phe728, Phe732, Leu762, Thr837, Ile868, Gly872, Phe942, Thr945, Tyr953, Leu975, Phe978, Ser979, Val982, Gly984, Ala985, Met986, Gly989, Gln990, and Ser993 (Aller, S. G. et al., Science, 2009, 323:1718-1722). A grid map was chosen to cover these residues. Three independent docking calculations for pomiferin and Rho123 were conducted with 2,500,000 evaluations and 250 runs using Lamarckian Genetic Algorithm. The lowest binding energies (LBE) and predicted inhibition constants were obtained from the docking log files (dlg) and mean±SD values were calculated. For visualization of the docking results, Visual Molecular Dynamics (VMD) were used. VMD software was developed with NIH support by the Theoretical and Computational Biophysics group at the Beckman Institute, University of Illinois at Urbana-Champaign. For co-docking calculations, Rho123 and pomiferin were selected to evaluate the effect of pre-docked compound on binding energies and docking pose.

Figure 1B:
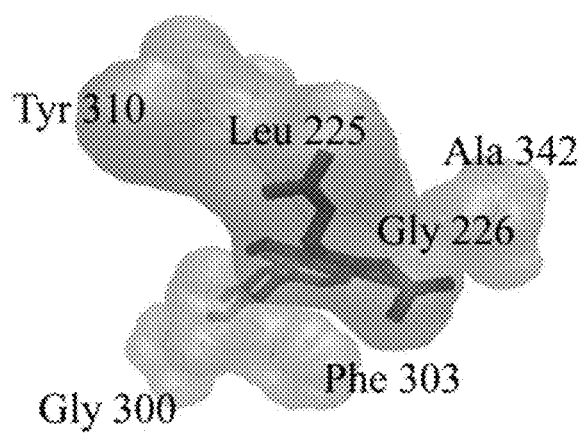
Figure 4A:
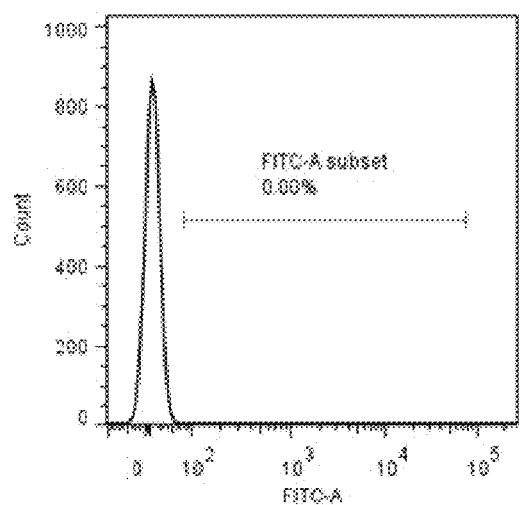
FIGS. 4A through 4G show curves obtained with flow cytometry analysis of a Rho123 efflux assay in MCF-7 taxol/doxorubicin sensitive breast cancer cells. These cancer cells were treated with Rho123 dye in the presence of the P-glycoprotein inhibitor verapamil (10 µM) or pomiferin with 5 µM, 10 µM, 15 µM or 20 µM compared to Rho123 control and an unstained group.
Figure 4B:
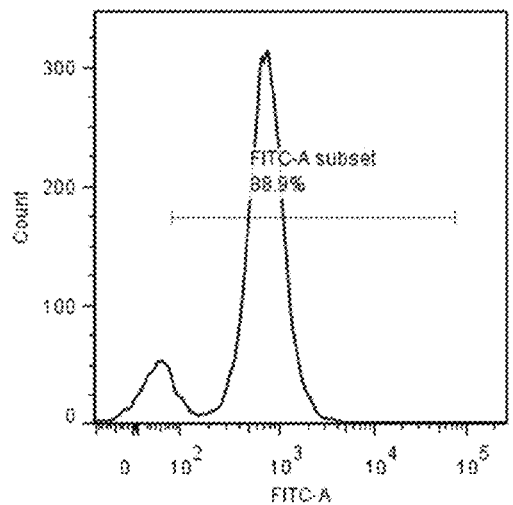
Figure 4C:
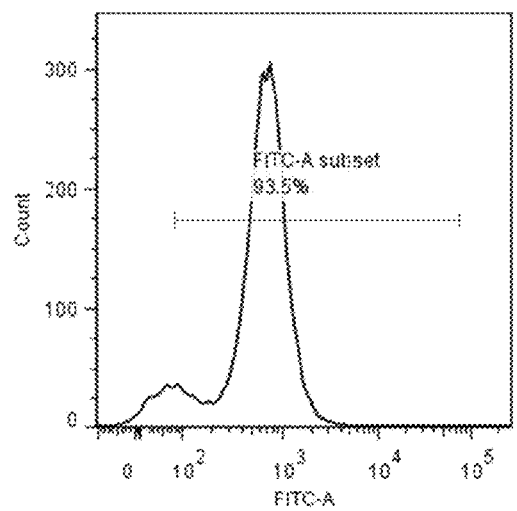
Figure 4D:
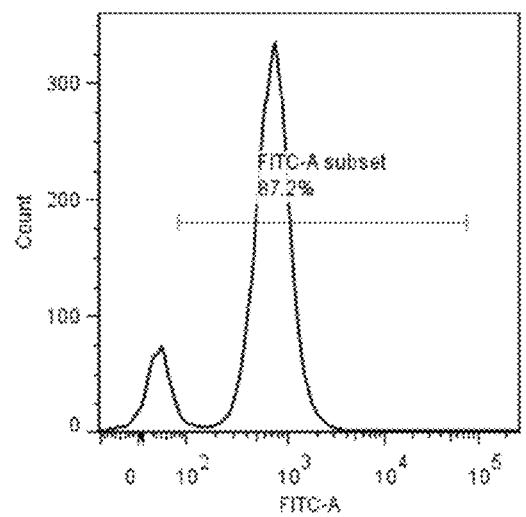
Figure 4E:
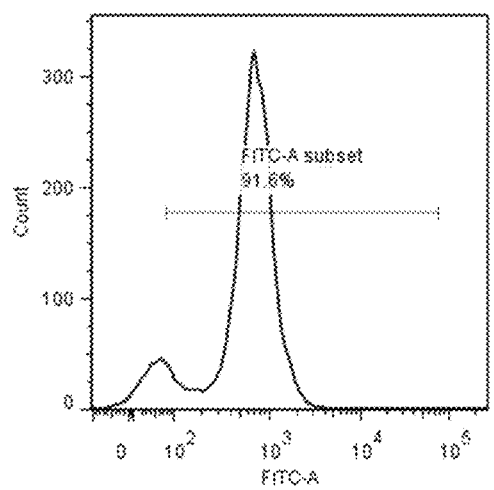
Figure 4F:
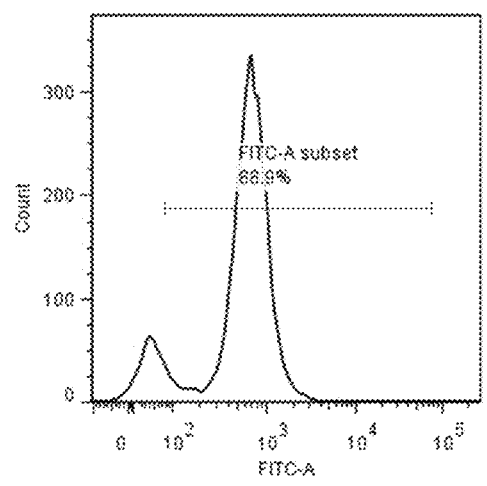
Figure 4G:
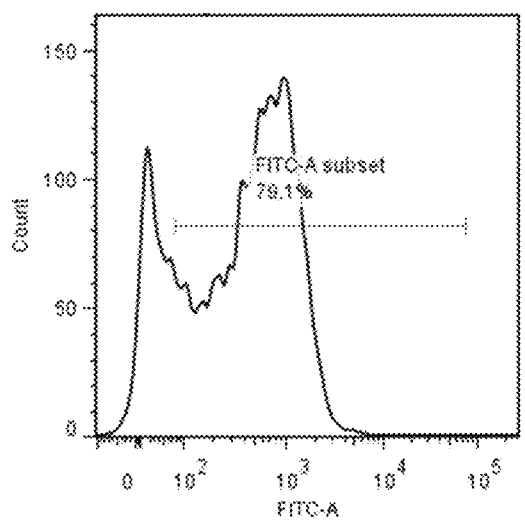
Figure 4H:
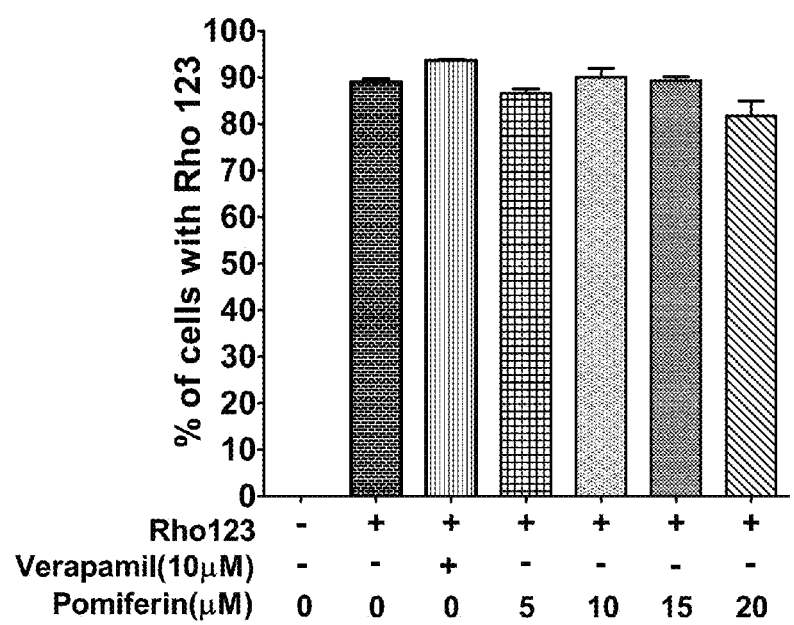
FIG. 4H is a bar chart showing the percentage of cells with Rho123 in verapamil- or pomiferin-treated MCF-7 taxol/doxorubicin sensitive breast cancer cells compared to Rho123 control and an unstained group.
Figure 5A:
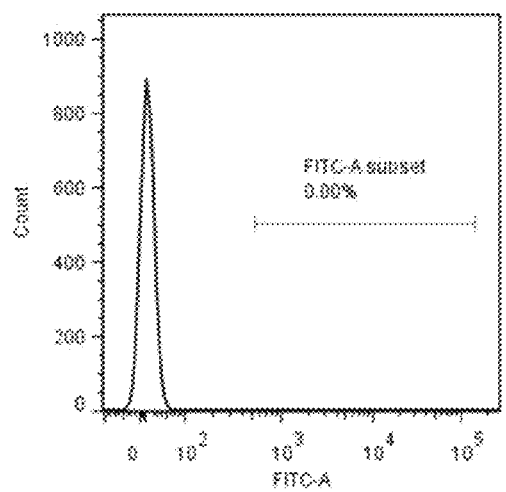
FIGS. 5A through 5G show curves obtained with flow cytometry analysis of a Rho123 efflux assay in MCF-7 taxol-resistant breast cancer cells. These cancer cells were treated with Rho123 dye in the presence of the P-glycoprotein inhibitor verapamil (10 µM) or pomiferin with 5 µM, 10 µM, 15 µM or 20 µM compared to Rho123 control and an unstained group.
Figure 5B:
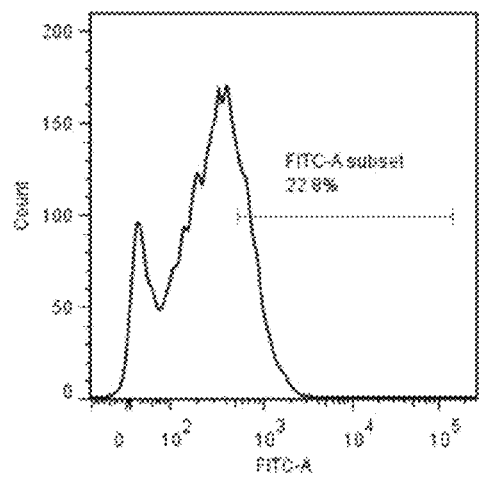
Figure 5C:
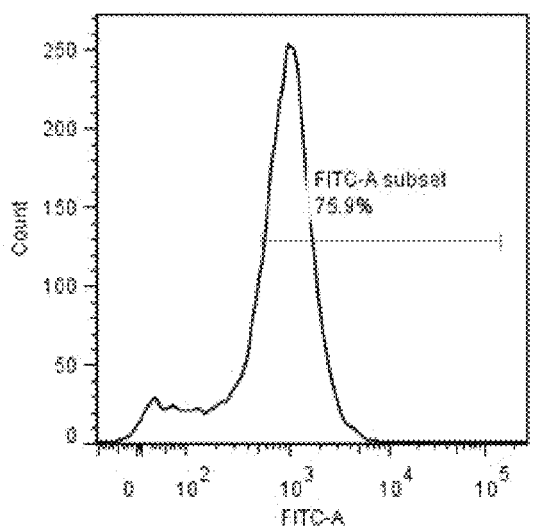
Figure 5D:
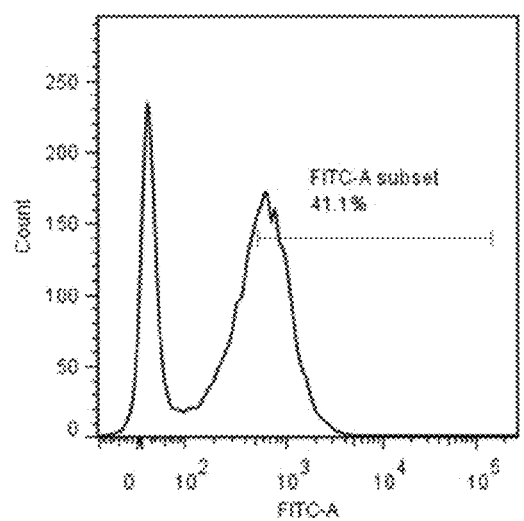
Figure 5E:
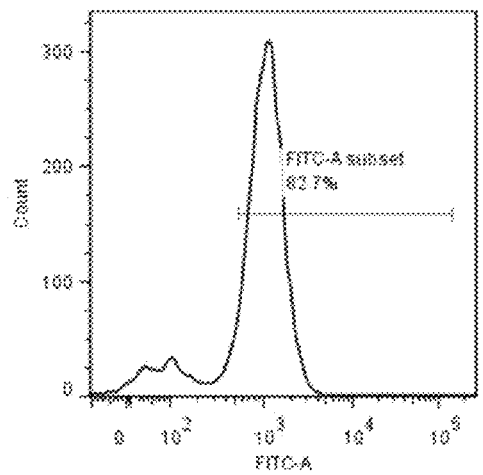
Figure 5F:
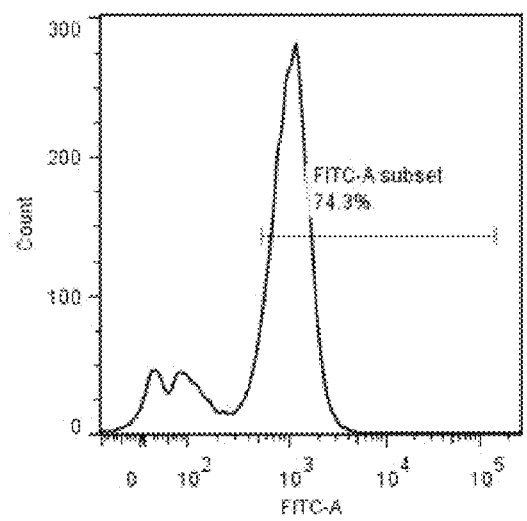
Figure 5G:
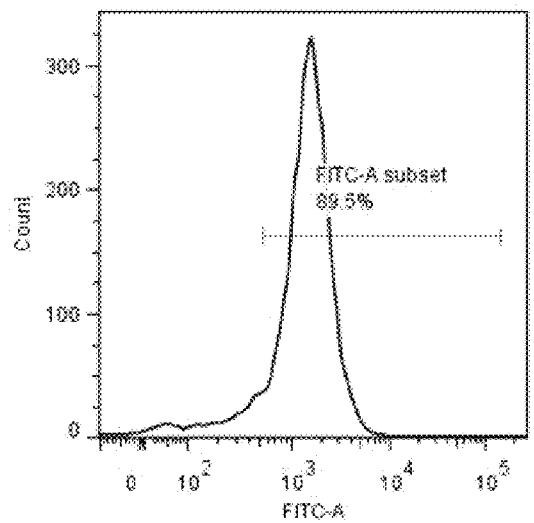
Figure 5H:
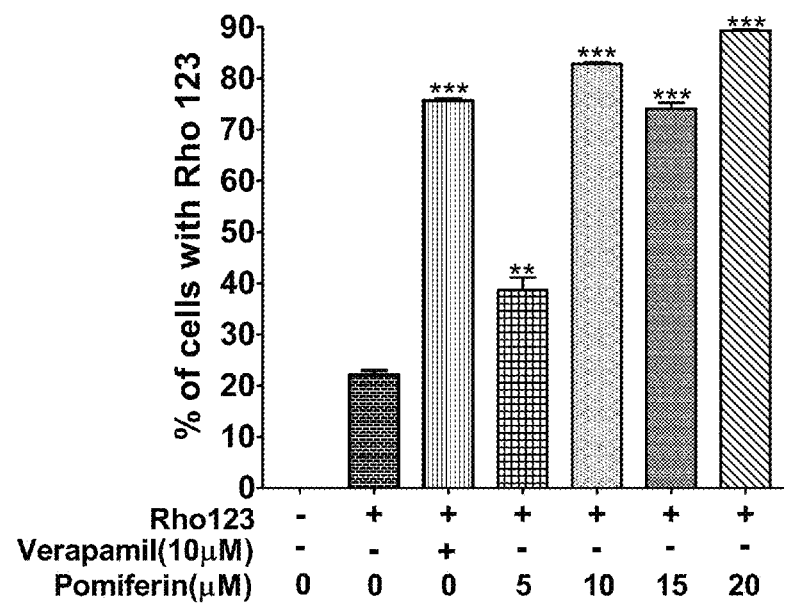
FIG. 5H is a bar chart showing the percentage of cells with Rho123 in verapamil- or pomiferin-treated MCF-7 taxol-resistant breast cancer cells compared to Rho123 control and an unstained group.
Figure 6A:
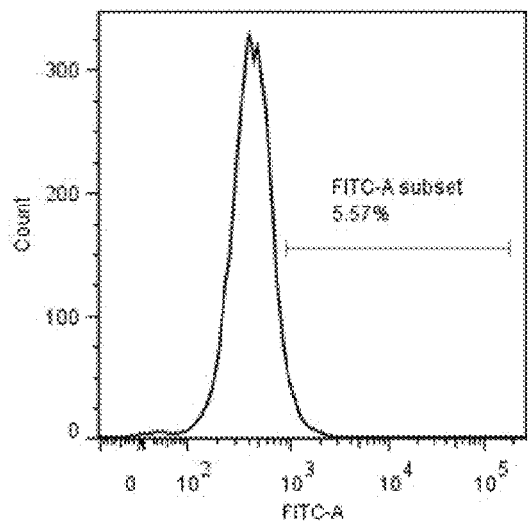
FIGS. 6A through 6G show curves obtained with flow cytometry analysis of a Rho123 efflux assay in MCF-7 doxorubicin-resistant breast cancer cells. These cancer cells were treated with Rho123 dye in the presence of the P-glycoprotein inhibitor verapamil (10 µM) or pomiferin with 5 µM, 10 µM, 15 µM or 20 µM compared to Rho123 control and an unstained group.
Figure 6B:
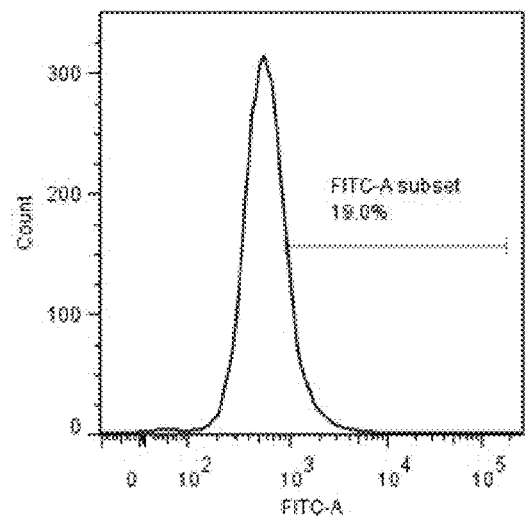
Figure 6C:
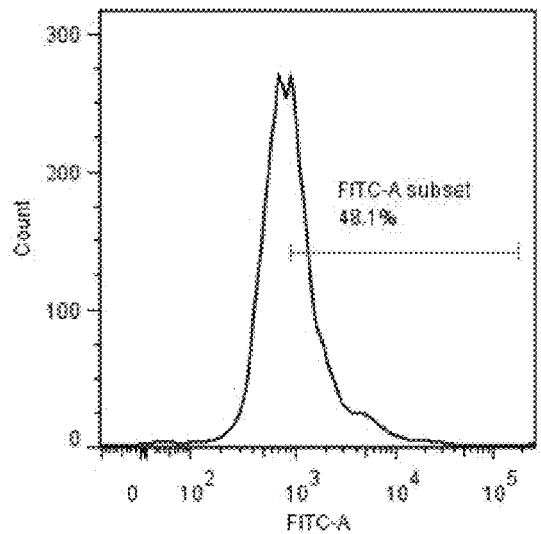
Figure 6D:
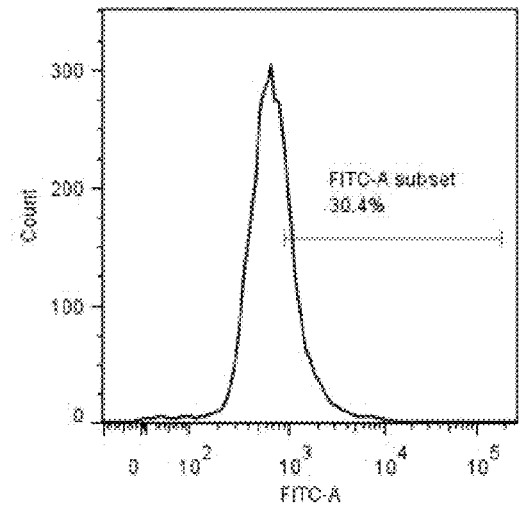
Figure 6E:
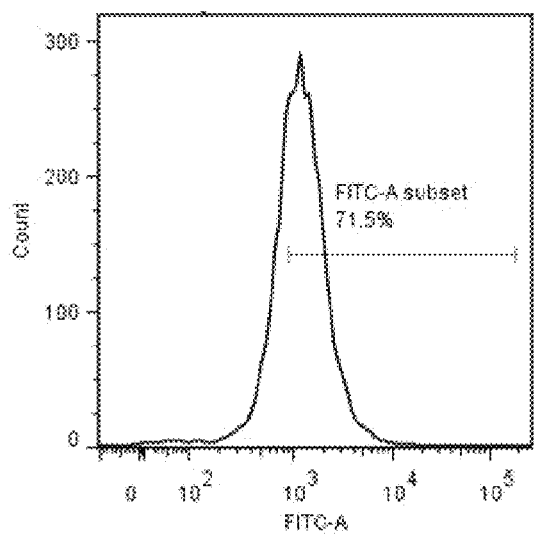
Figure 6F:
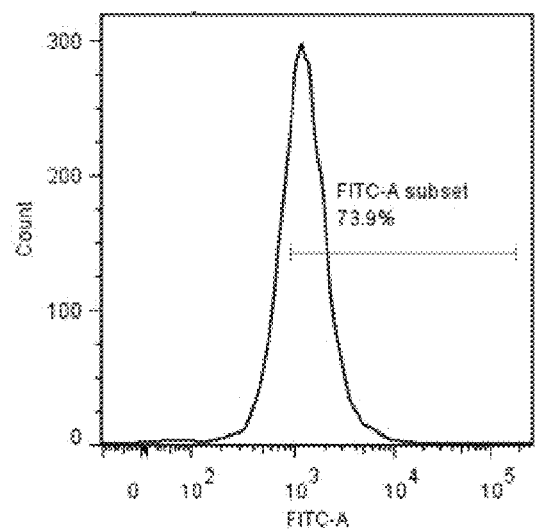
Figure 6G:
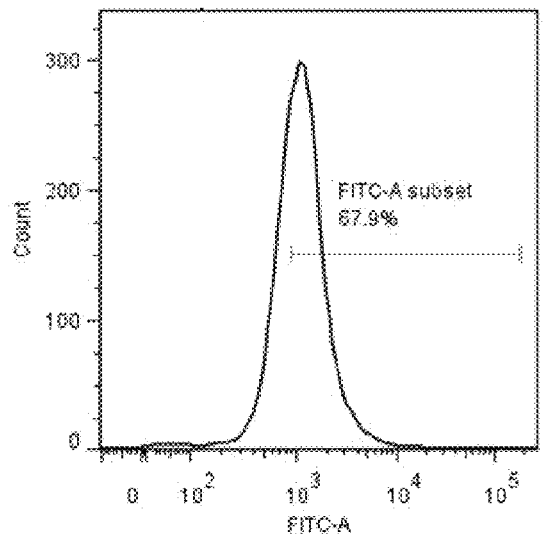
Figure 6H:
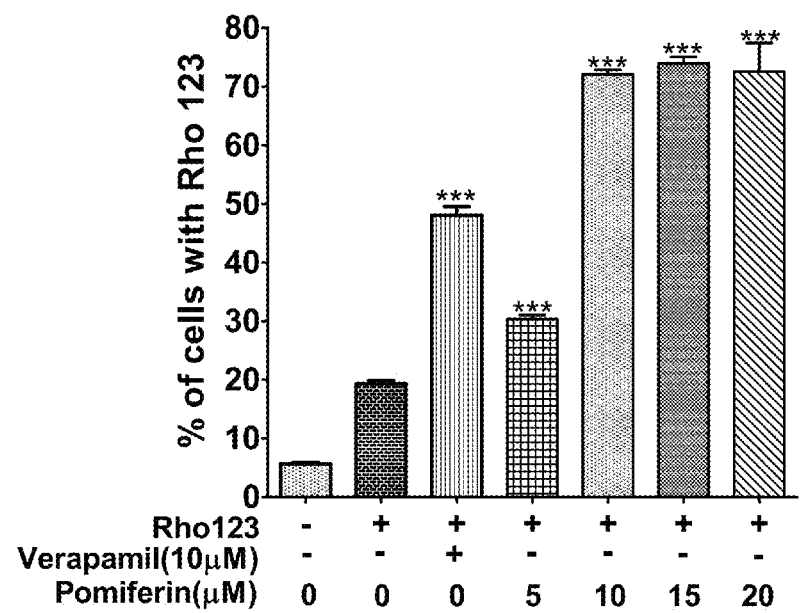
FIG. 6H is a bar chart showing the percentage of cells with Rho123 in verapamil- or pomiferin-treated MCF-7 doxorubicin-resistant breast cancer cells compared to Rho123 control and an unstained group.
Figure 7A:
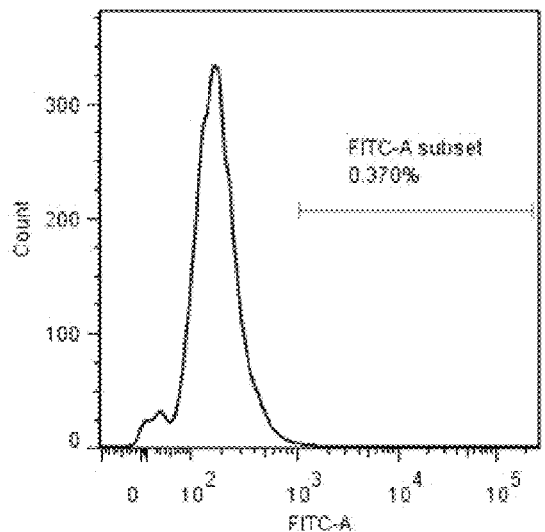
FIGS. 7A through 7G show curves obtained with flow cytometry analysis of a Rho123 efflux assay in A549 taxol-resistant lung cancer cells. These cancer cells were treated with Rho123 dye in the presence of the P-glycoprotein inhibitor verapamil (10 µM) or pomiferin with 5 µM, 10 µM, 15 µM or 20 µM compared to Rho123 control and an unstained group.
Figure 7B:
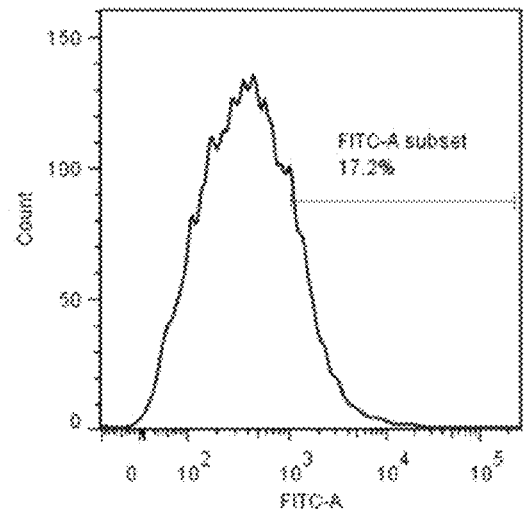
Figure 7C:
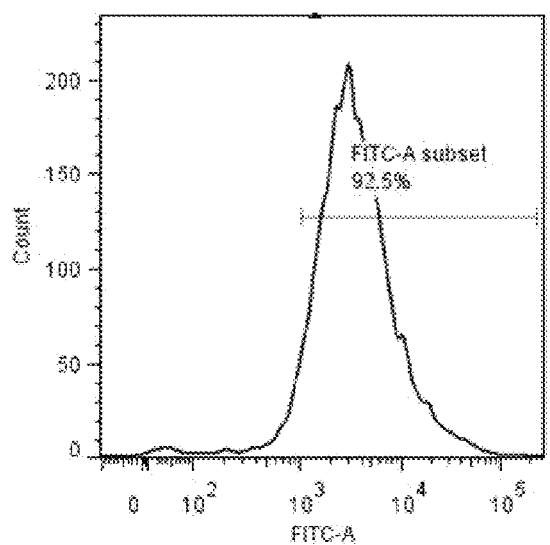
Figure 7D:
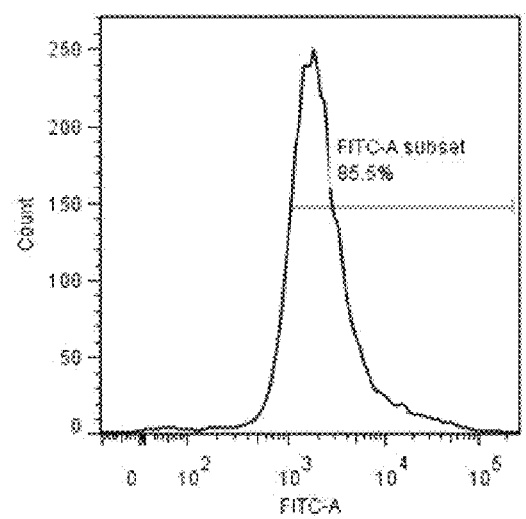
Figure 7E:
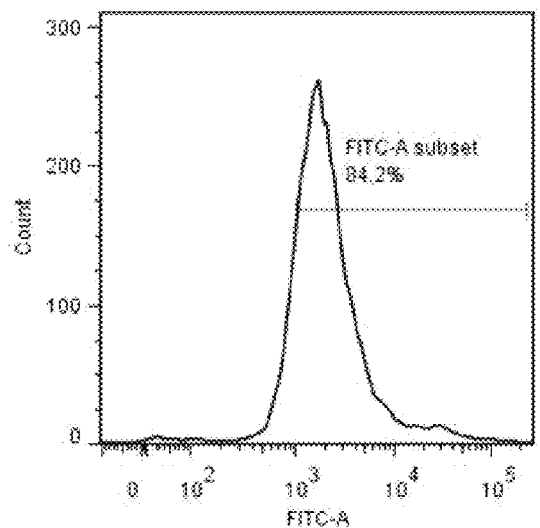
Figure 7F:
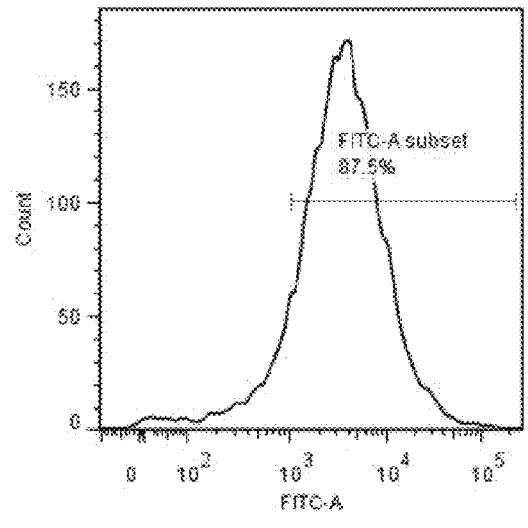
Figure 7G:
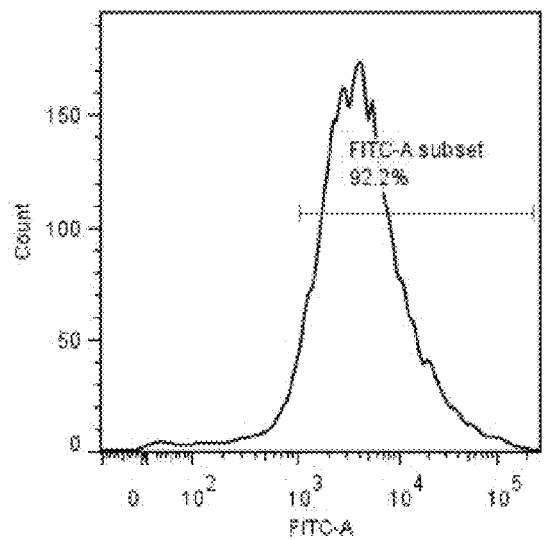
Figure 7H:
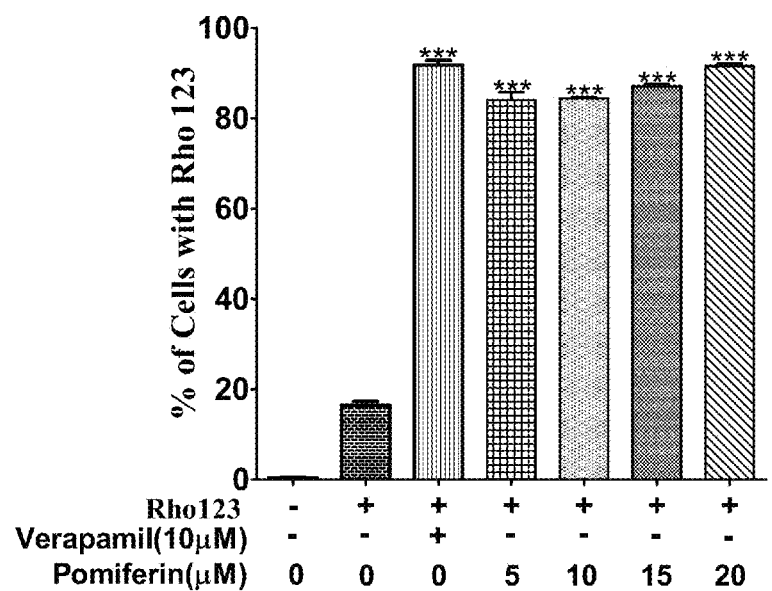
FIG. 7H is a bar chart showing the percentage of cells with Rho123 in verapamil- or pomiferin-treated A549 taxol-resistant lung cancer cells compared to Rho123 control and an unstained group.
Figure 8A:
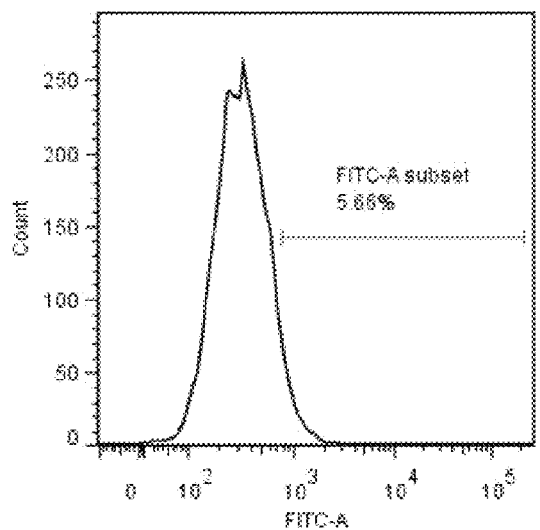
FIGS. 8A through 8G show curves obtained with flow cytometry analysis of a Rho123 efflux assay in HCT-8 taxol-resistant colon cancer cells. These cancer cells were treated with Rho123 dye in the presence of the P-glycoprotein inhibitor verapamil (10 µM) or pomiferin with 5 µM, 10 µM, 15 µM or 20 µM compared to Rho123 control and an unstained group.
Figure 8B:
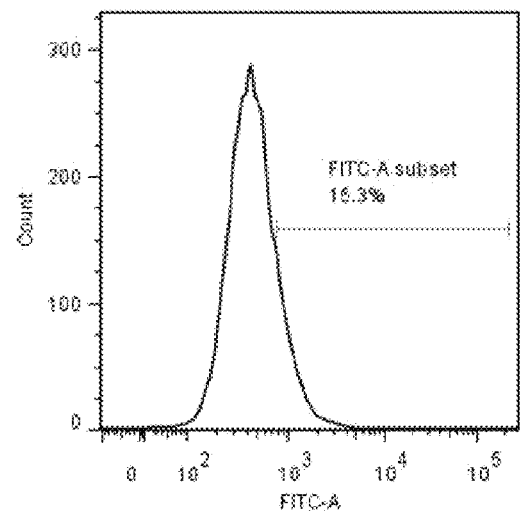
Figure 8C:
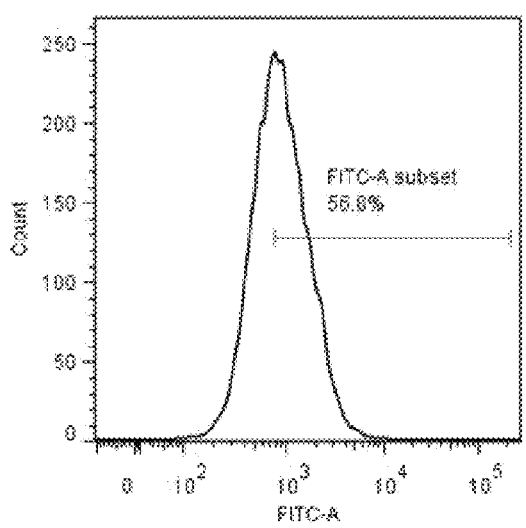
Figure 8D:
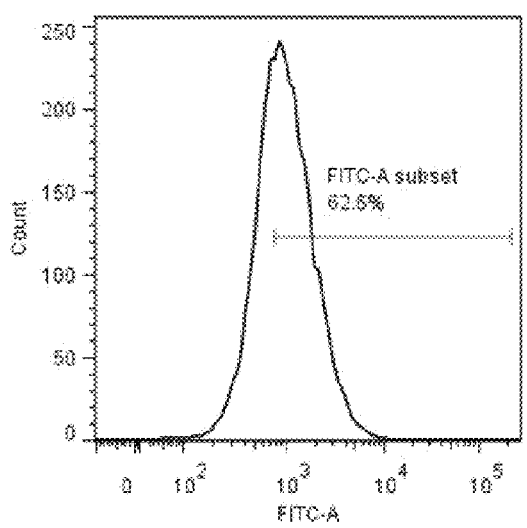
Figure 8E:
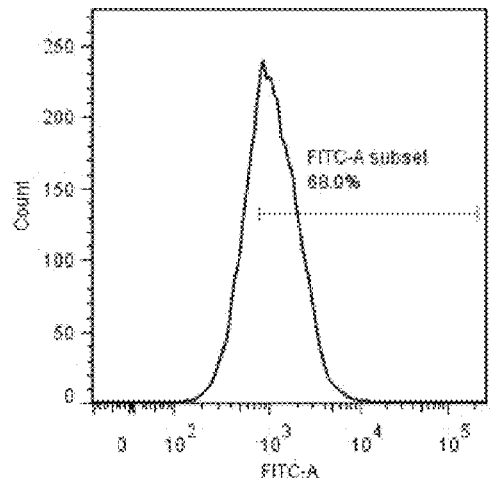
Figure 8F:
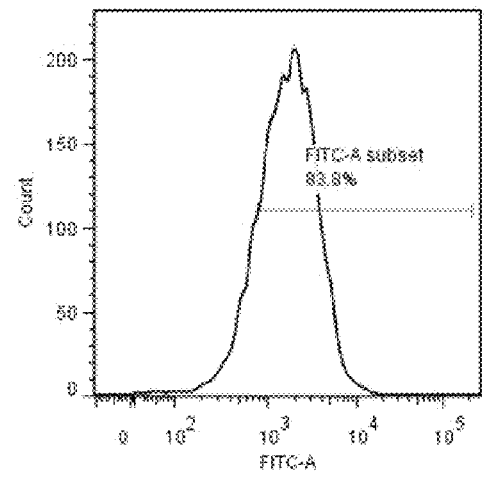
Figure 8G:
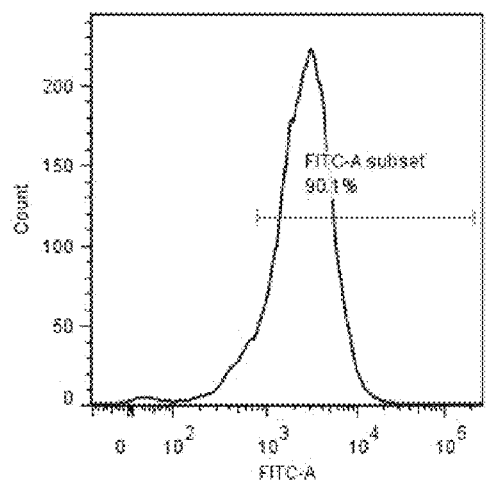
Figure 8H:
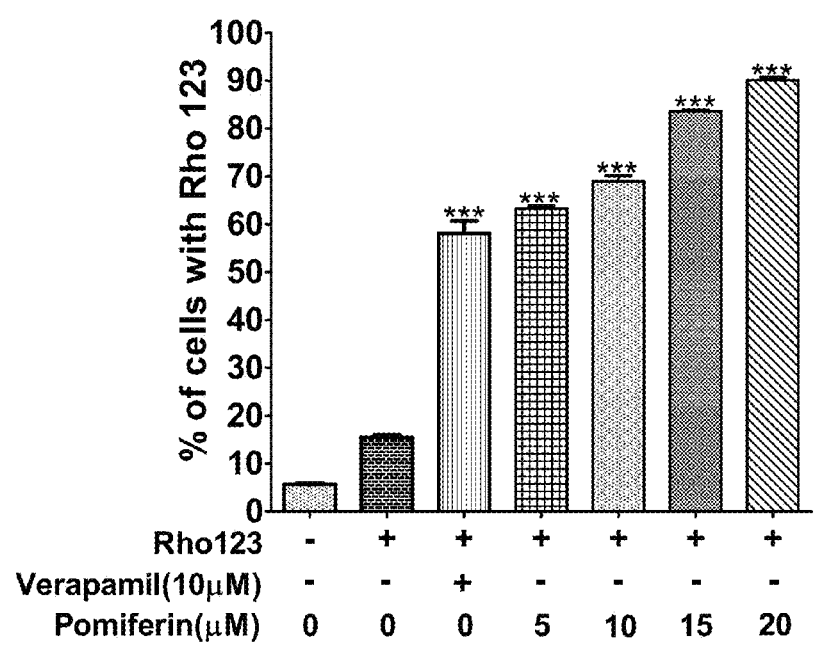
FIG. 8H is a bar chart showing the percentage of cells with Rho123 in verapamil- or pomiferin-treated HCT-8 taxol-resistant colon cancer cells compared to Rho123 control and an unstained group.
Figure 9A:
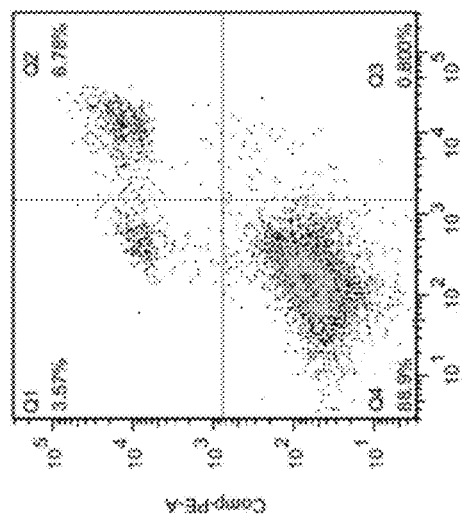
FIGS. 9A through 9J show the patterns obtained with flow cytometry analysis of cell death in A549 taxol-resistant lung cancer cells. These cancer cells were treated with 1 µM, 2 µM, 5 µM or 10 µM of pomiferin in the presence or absence of taxol (40 µM) and compared to a control group.
Figure 9B:
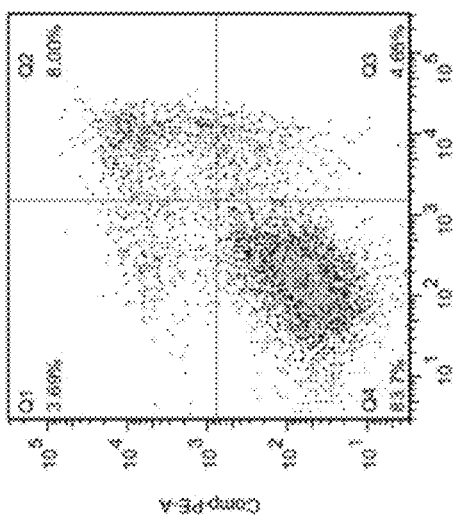
Figure 9C:
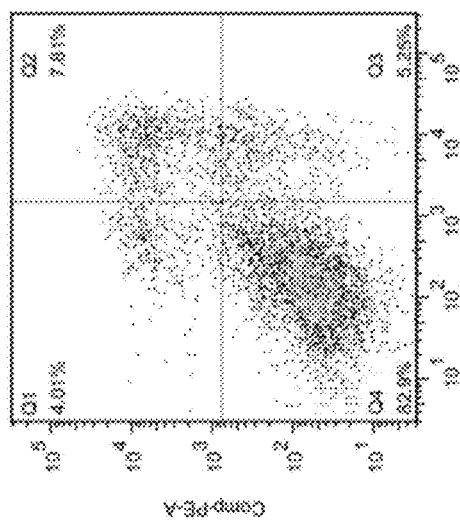
Figure 9D:
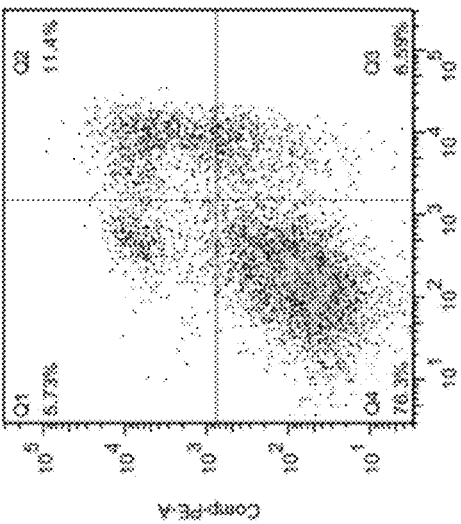
Figure 9E:
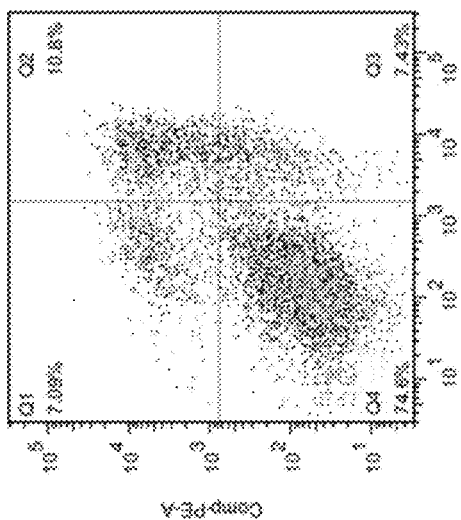
Figure 9H:
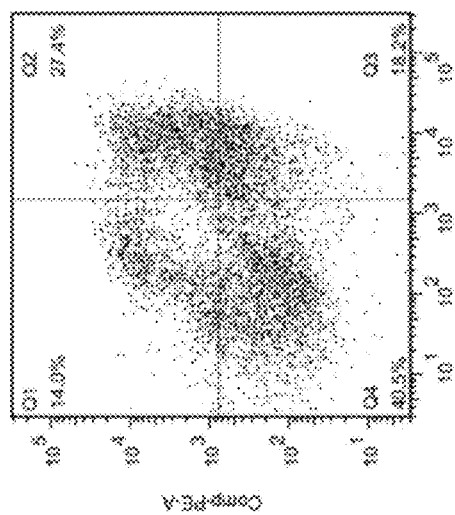
Figure 9G:
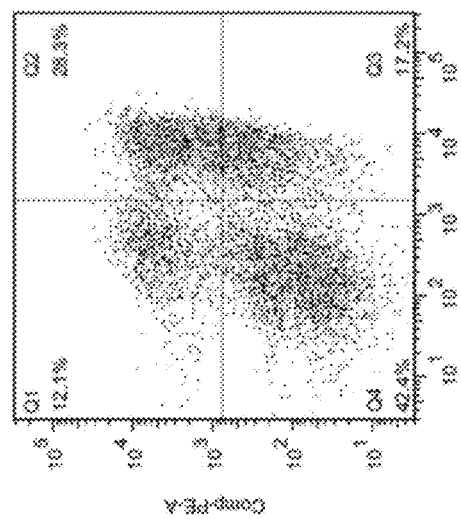
Figure 9J:
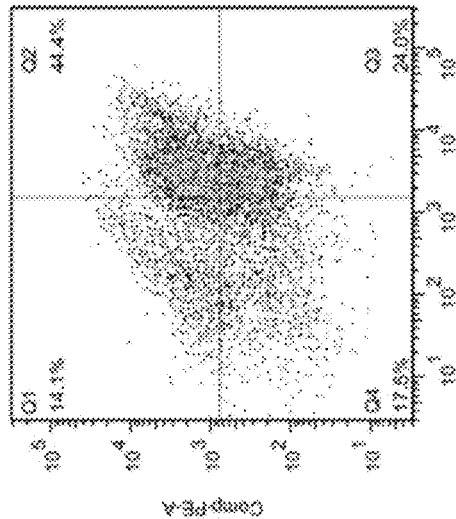
Figure 9F:
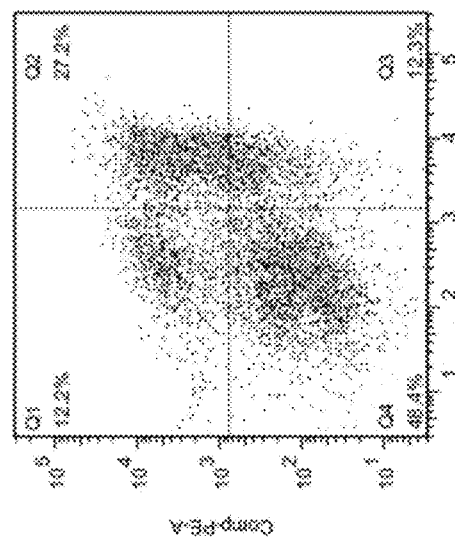
Figure 9I:
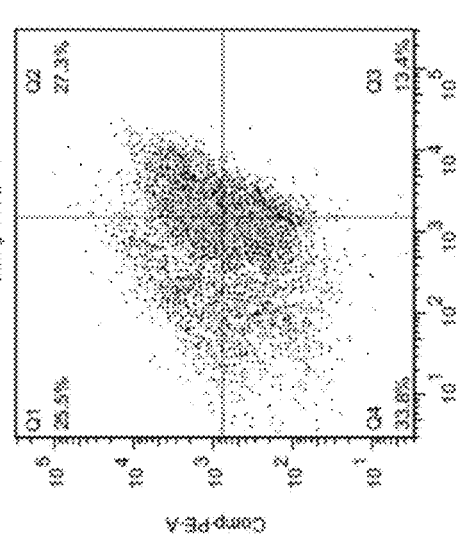
Figure 9K:
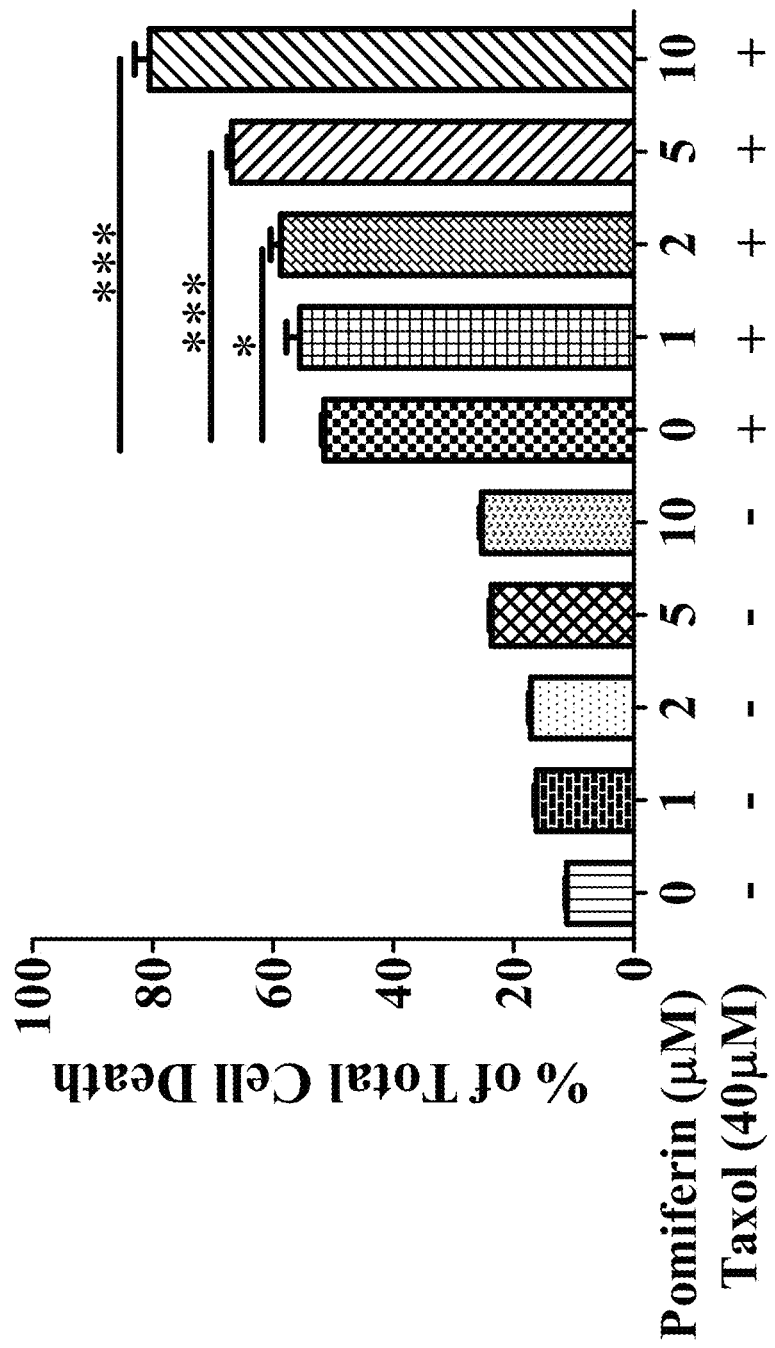
FIG. 9K is a bar chart showing the percentages of cell death in A549 taxol-resistant lung cancer cells in the presence or absence of pomiferin and taxol compared to a control group.
Figure 10A:
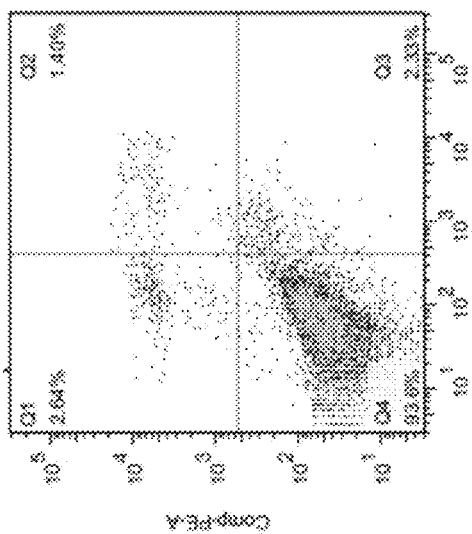
FIG. 10A through 10J refer to a flow cytometry analysis of cell death in HCT-8 taxol-resistant colon cancer cells. These cancer cells were treated with 1 µM, 2 µM, 5 µM or 10 µM of pomiferin in the presence or absence of taxol (40 µM) and compared to a control group.
Figure 10B:
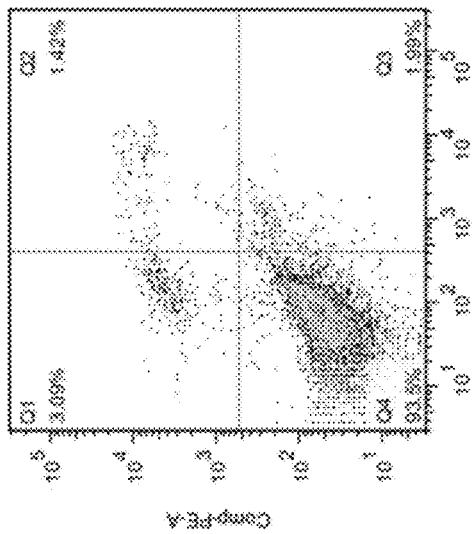
Figure 10C:
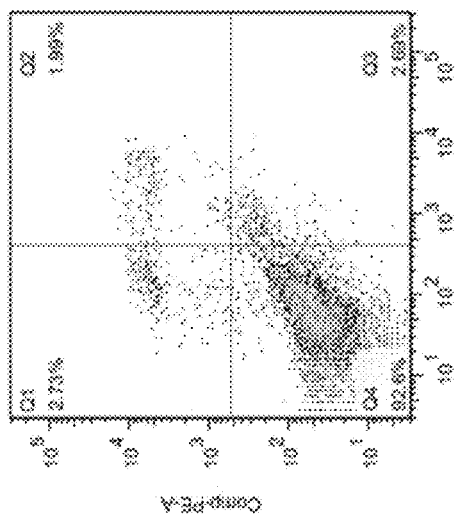
Figure 10D:
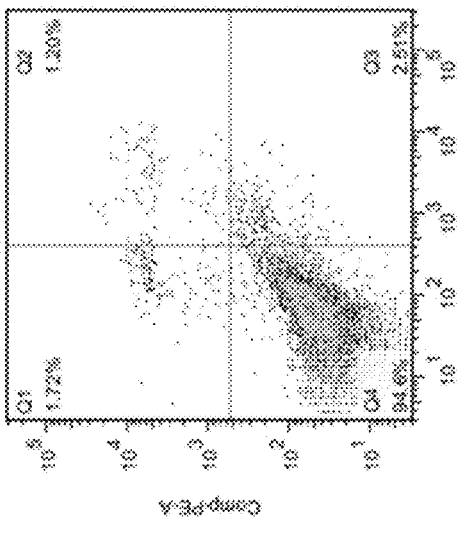
Figure 10E:
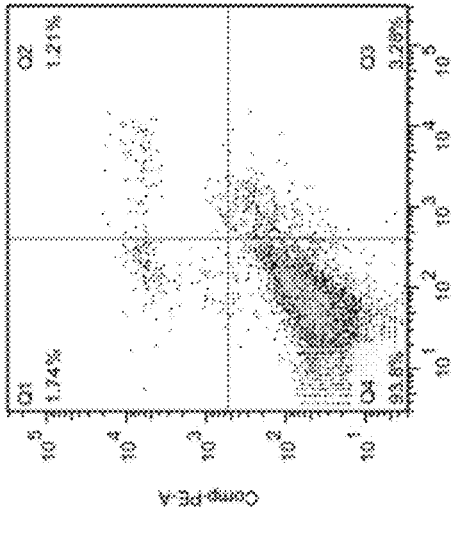
Figure 10F:
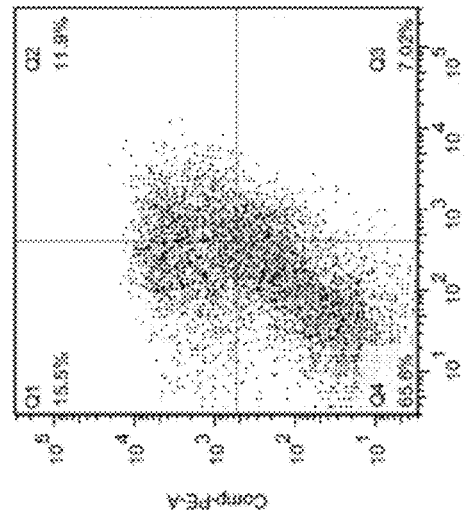
Figure 10G:
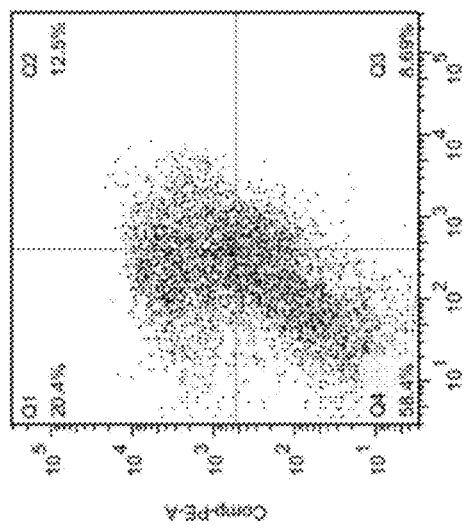
Figure 10H:
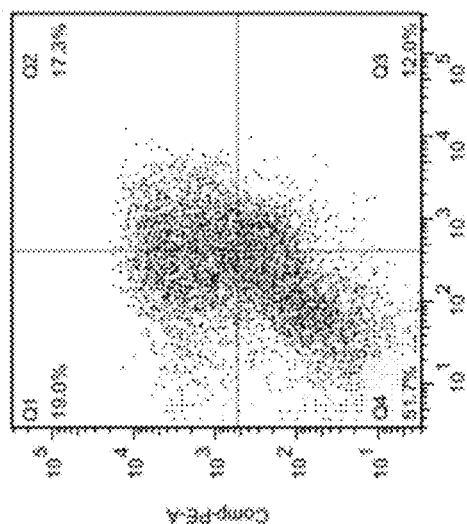
Figure 10I:
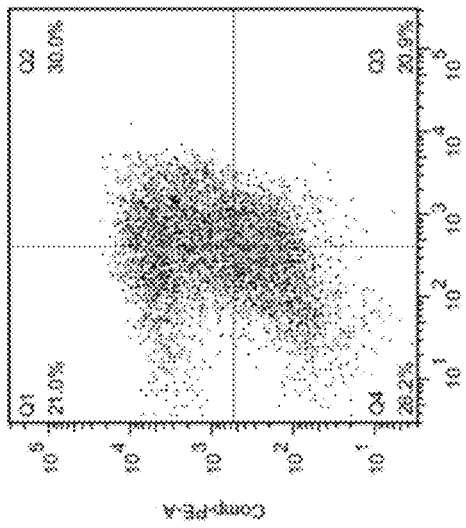
Figure 10J:
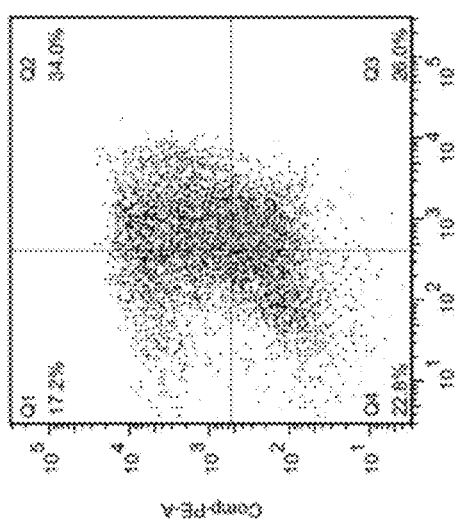
Figure 10K:
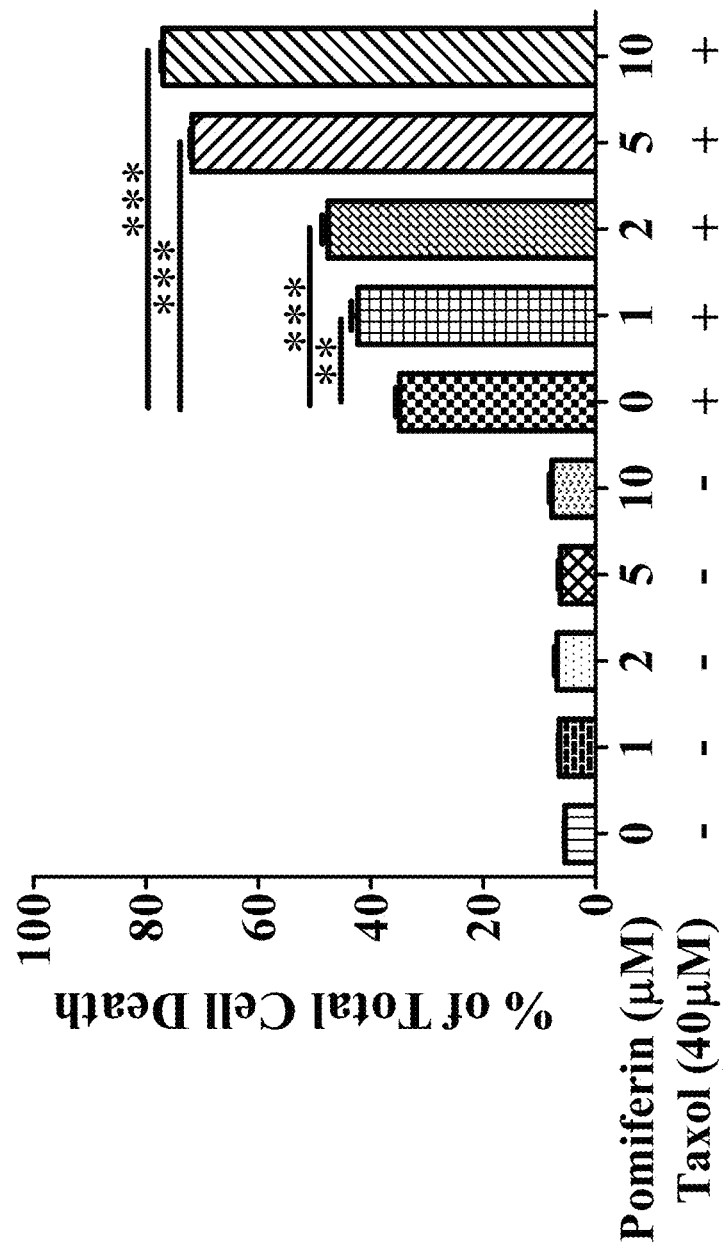
FIG. 10K is a bar chart showing the percentages of cell death in HCT-8 taxol-resistant colon cancer cells in the presence or absence of pomiferin and taxol compared to a control group.
Figure 11A:
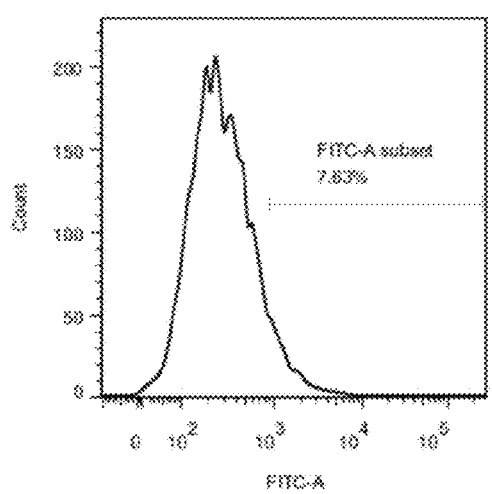
FIGS. 11A through 11I show a comparison between pomiferin and further prenylated isoflavones of the present invention obtained with flow cytometry analysis of a Rho123 efflux assay in A549 taxol-resistant lung cancer cells. These cancer cells were treated with Rho123 dye in the presence of the P-glycoprotein inhibitor verapamil (10 µM) or in the presence of 10 µM pomiferin, pomiferin 3',4'-dimethyl ether, pomiferin trimethyl ether, isopomiferin, osajin, osajin 4'-methyl ether and isoosajin compared to Rho123 control.
Figure 11B:
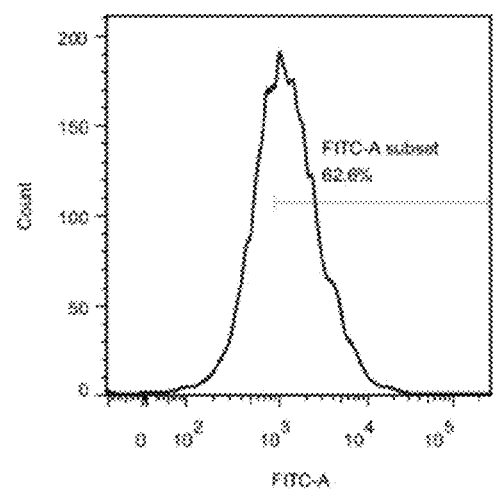
Figure 11C:
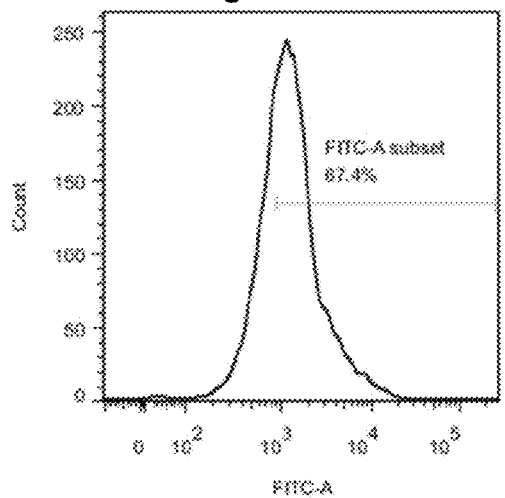
Figure 11D:
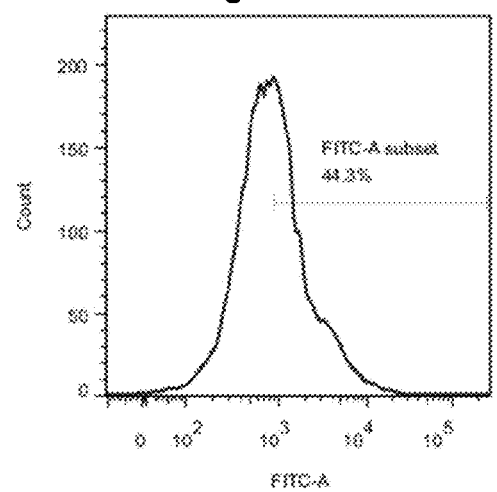
Figure 11E:
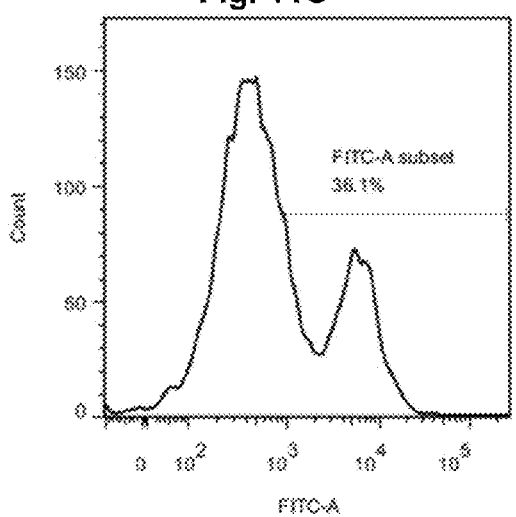
Figure 11F:
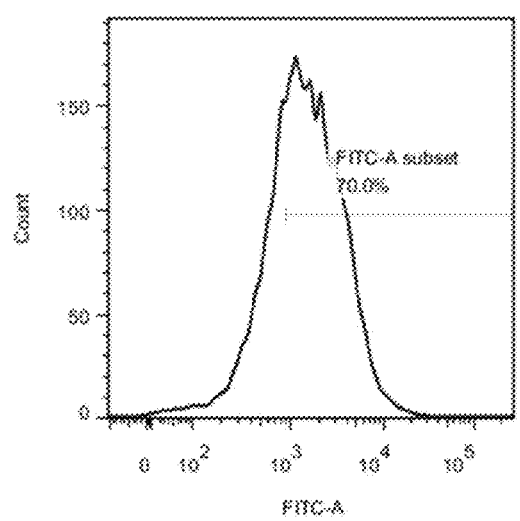
Figure 11G:
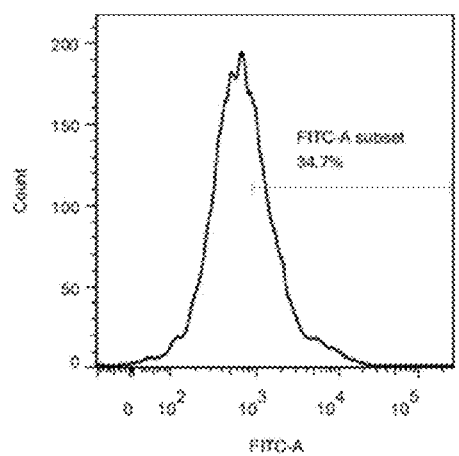
Figure 11H:
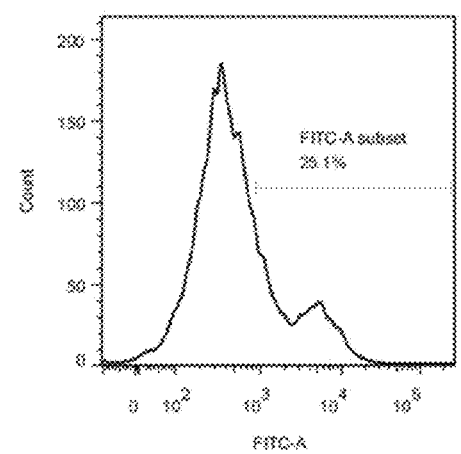
Figure 11I:
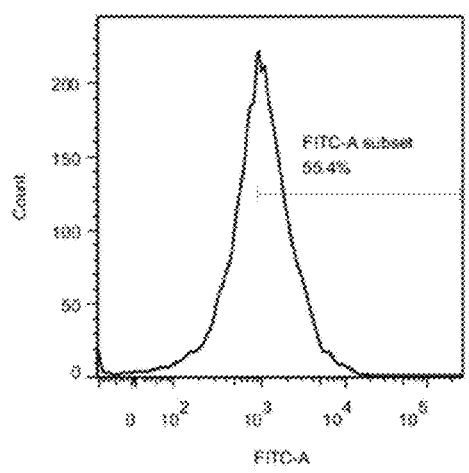
Figure 11J:
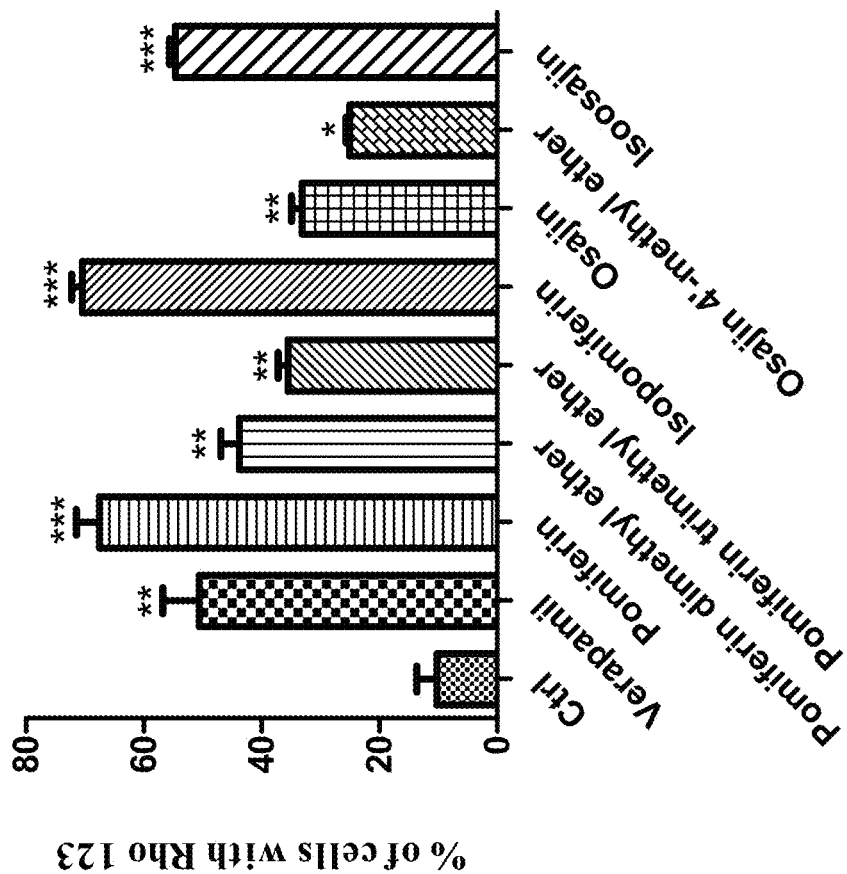
FIG. 11J is a bar chart showing the percentage of cells with Rho123 in verapamil- or pomiferin-treated A549 taxol-resistant lung cancer cells as well as in A549 taxol-resistant lung cancer cells treated with further prenylated isoflavones of the present invention compared to Rho123 control.

Pomiferin showed similar docking pose and higher LBE value (−9.64±0.02 kcal/mol) than Rho123 (−8.61±0.01 kcal/mol) on the drug binding pocket of P-glycoprotein (FIG. 1A to 1B). In order to assess whether pre-docking of Rho123/pomiferin could interfere with LBE value or docking pose, dockings of Rho123 and pomiferin to complexes of P-glycoprotein pre-docked with either of them were performed. When Rho123 was pre-docked (FIG. 2A to 2C), pomiferin can still bind with a high affinity (−8.62±0.08 kcal/mol) on a nearby site at the drug binding pocket. Rho123 docked to a neighboring site with a lower affinity (−7.91±0.01 kcal/mol) when pomiferin was bound on P-glycoprotein (FIG. 3A to 3C). These results show that pomiferin docked to the drug binding pocket with higher affinity than the known P-glycoprotein substrate Rho123, which proves that it is suitable as potent P-glycoprotein inhibitor. Results are further detailed in tables 1 to 3.

TABLE 1

Results of molecular docking studies with either pomiferin or Rho123

| P-gp docking | LBE (kcal/mol) | pKi (μM) | Interacting residues | Residues forming H-bond |
|---|---|---|---|---|
| pomiferin | −9.64 ± 0.02 | 0.09 ± 0.00 | Leu225, Gly226, Ala229, Ala230, Gly300, Phe303, Leu304, Ile306, Tyr307, Tyr310, Ala342, Phe343 | Gly300, Phe303 |

TABLE 1-continued

Results of molecular docking studies
with either pomiferin or Rho123

| P-gp docking | LBE (kcal/mol) | pKi (μM) | Interacting residues | Residues forming H-bond |
|---|---|---|---|---|
| Rho123 | −8.61 ± 0.01 | 0.49 ± 0.01 | Ser222, Leu225, Phe303, Lau304, Ile306, Tyr307, Tyr310, Leu339, Ala342, Phe343 | — |

TABLE 2

Results of molecular docking studies with pre-docked Rho123

| P-gp docking | LBE (kcal/mol) | pKi (μM) | Interacting residues | Residues forming H-bond |
|---|---|---|---|---|
| pomiferin | −8.62 ± 0.08 | 0.48 ± 0.07 | Val133, Trp136, Ile190, Gly191, Leu879, Ala883, Asp886, Leu934, Phe938, Phe942 | Asp886, Lys934 |

TABLE 3

Results of molecular docking studies with pre-docked pomiferin

| P-gp docking | LBE (kcal/mol) | pKi (μM) | Interacting residues | Residues forming H-bond |
|---|---|---|---|---|
| Rho123 | −7.91 ± 0.01 | 1.60 ± 0.01 | Leu861, Ile864, Val865, Ile868, Met948, Ser952, Tyr953, Cys956, Val981 | — |

Example 2

Effects of Pomiferin in MCF-7 Taxol/Doxorubicin-Sensitive Breast Cancer Cells

A Rho123 efflux assay has been carried out. Drug-sensitive MCF-7 breast cancer cells having no P-glycoprotein expression were seeded in a 6 well-plate at a final concentration of $2 \times 10^5$ cells per well and cultured for 24 h at 37° C. in an atmosphere containing 5% $CO_2$. At confluence, 3 mL fresh medium with or without 5 μM, 10 μM, 15 μM and 20 μM pomiferin, or 10 μM verapamil (known P-glycoprotein inhibitor) was added and incubated further at 37° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 μL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

Rho123 dye is a known substrate of P-glycoprotein. Cancer cells, mainly multidrug-resistant cancer cells, which are P-glycoprotein-dependent will efflux the Rho123 dye from the cells, while the cancer cells, mainly drug-sensitive cancer cells, without P-glycoprotein expression will retain the Rho123 dye inside the cells. As shown in FIG. 4A to FIG. 4H, Rho123 dye staining demonstrated a markedly increase of fluorescence signal in taxol/doxorubicin-sensitive MCF-7 cancer cells, revealing that those drug-sensitive cancer cells without P-glycoprotein expression would retain most of the Rho123 dye inside the cells. However, addition of P-gp inhibitor verapamil or pomiferin showed no difference in fluorescence signal compared with Rho123 stained cells. Taken together, the findings suggest that drug-sensitive cancer cells without P-glycoprotein expression usually retain the Rho123 dye or other chemotherapeutic compounds like taxol or doxorubicin inside the cells.

Example 3

Effects of Pomiferin in MCF-7 Taxol-Resistant Breast Cancer Cells

A Rho123 efflux assay has been carried out. MCF-7 taxol-resistant breast cancer cells were seeded in a 6 well-plate at a final concentration of $2 \times 10^5$ cells per well and cultured for 24 h at 37° C. in an atmosphere containing 5% $CO_2$. At confluence, 3 mL fresh media with or without 5 μM, 10 μM, 15 μM and 20 μM pomiferin, or 10 μM verapamil (known P-glycoprotein inhibitor) was added and incubated further at 37° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 μL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

As shown in FIG. 5A to FIG. 5H, Rho123 dye staining in taxol-resistant breast cancer cells only yielded 20% of cell population with fluorescence signal, suggesting that P-glycoprotein in these taxol-resistant cancer cells effectively pumped out the Rho123 dye from the cells. However, addition of the P-glycoprotein inhibitor verapamil significantly suppressed the P-glycoprotein activity, leading to markedly increase of Rho123 fluorescence signal in cells. Meanwhile, pomiferin dose-dependently inhibited the P-glycoprotein activity, thereby increased the Rho123 accumulation in taxol-resistant cancer cells. Collectively, these results confirm that pomiferin is a potent P-glycoprotein inhibitor at least as effective as verapamil, as it advantageously inhibits P-glycoprotein functional activity in MCF-7 taxol-resistant breast cancer cells.

Example 4

Effects of Pomiferin in MCF-7 Doxorubicin-Resistant Breast Cancer Cells

A Rho123 efflux assay has been carried out. MCF-7 doxorubicin-resistant breast cancer cells were seeded in a 6 well-plate at a final concentration of $2 \times 10^5$ cells per well and cultured for 24 h at 37° C. in an atmosphere containing 5% $CO_2$. At confluence, 3 mL fresh media with or without 5 μM, 10 μM, 15 μM and 20 μM pomiferin, or 10 μM verapamil (known P-glycoprotein inhibitor) was added and incubated further at 37° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 μL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

As shown in FIG. 6A to FIG. 6H, Rho123 dye staining in doxorubicin-resistant breast cancer cells only yielded 20% of cell population with fluorescence signal, suggesting that P-glycoprotein in these doxorubicin-resistant cancer cells effectively pumped out the Rho123 dye from the cells. However, addition of the P-glycoprotein inhibitor verapamil significantly suppressed the P-glycoprotein functional activity, leading to markedly increase of Rho123 fluorescence signal in cells. Consistently, pomiferin dose-dependently inhibited the P-glycoprotein activity, thereby increased the Rho123 accumulation in doxorubicin-resistant cancer cells. Collectively, these results confirm that pomiferin is exceptionally suitable to suppress Rho123 exclusion in other drug-resistant cancer cell types, too.

Example 5

Effects of Pomiferin in A549 Taxol-Resistant Lung Cancer Cells and HCT-8 Taxol-Resistant Colon Cancer Cells A Rho123 efflux assay has been carried out. A549 taxol-resistant lung cancer cells or HCT-8 taxol-resistant colon cancer cells were seeded in 6 well-plates at a final concentration of 2×10$^5$ cells per well and cultured for 24 h at 37° C. in an atmosphere containing 5% $CO_2$. At confluence, 3 mL fresh media with or without 5 μM, 10 μM, 15 μM and 20 μM pomiferin, or 10 μM verapamil (known P-glycoprotein inhibitor) was added and incubated further at 37° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 μL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

As shown in FIG. 7A to FIG. 7H and FIG. 8A to FIG. 8H, Rho123 dye staining in taxol-resistant lung or colon cancer cells only yielded less than 20% of cell population with fluorescence signal, suggesting that P-glycoprotein in other origins of taxol-resistant cancer cells effectively pumped out the Rho123 dye from the cells. Addition of the P-glycoprotein inhibitor verapamil significantly suppressed the P-glycoprotein activity, leading to markedly increase of Rho123 fluorescence signal in cells. Concomitantly, in both, lung and colon taxol-resistant cancers, pomiferin dose-dependently inhibited the P-glycoprotein activity, thereby increased the Rho123 accumulation in these taxol-resistant cancer cells. Collectively, these results again confirm that pomiferin is exceptionally suitable able to suppress Rho123 exclusion in taxol-resistant cancer cells from different origins.

Example 6

Collateral Sensitivity of Pomiferin in Multidrug-Resistant Cancer Cells

Cell cultures and cytotoxicity assays have been carried out. Pomiferin is dissolved in DMSO at a final concentration of 100 mmol/L and stored at −20° C. Cytotoxicity is assessed using the 3-(4,5-dimethylthiazol-2-yl)-2,5-diphenyltetrazolium bromide assay. 4000 cells from MCF-7 drug-sensitive breast cancer cells, MCF-7 taxol/doxorubicin-resistant breast cancers cells, A549 drug-sensitive or taxol-resistant lung cancer cells and HCT-8 drug-sensitive or taxol-resistant colon cancer cells are seeded on 96-well plates per well. After overnight pre-incubation, the cells are exposed to different concentrations of pomiferin (0.039-100 μmol/L) or taxol, or doxorubicin for 3 days. Subsequently, 10 μL of MTT reagents is added to each well and incubated at 37° C. for 4 hours followed by the addition of 100 μL solubilization buffer (10% SDS in 0.01 mol/L HCl) and overnight incubation. Absorbance at 585 nm is determined from each well the next day. The percentage of cell viability is calculated using the following formula: Cell viability (%)=Cells number treated/Cells number DMSO control× 100. Data are obtained from three independent experiments. The resistant factor is calculated by dividing the $IC_{50}$ in resistant cells by its $IC_{50}$ against drug-sensitive cells.

MCF-7 doxorubicin-sensitive/-resistant cancer cells demonstrated a significant drug-resistant phenotype in response to doxorubicin treatment with 21.6 resistant factor, whereas pomiferin showed more cytotoxicity toward the doxorubicin-resistant breast cancer cells with a resistant factor 0.42 (table 4). Beside, MCF-7 taxol-sensitive/-resistant cancer cells demonstrated a marked resistance toward the taxol treatment with resistant factor over 5000, whereas pomiferin even showed more cytotoxic potency in taxol-resistant breast cancer cells (resistant factor: 0.76) (table 5). In other multidrug-resistant cancer cells, taxol exhibited a 1000 to 35300 resistant factor in A549 and HCT-8 taxol-resistant cancer cells respectively compared with their taxol-sensitive cells (table 6 and table 7). In contrast, pomiferin showed much better cytotoxic potency in both A549 and HCT-8 taxol-resistant cancer cells with resistant factor from 0.69 to 0.95 (table 6 and table 7). Collectively, these results confirm that pomiferin exhibits collateral sensitivity toward the multidrug-resistant cancer cells via direct inhibition of P-glycoprotein.

TABLE 4

$IC_{50}$ of doxorubicin and pomiferin in doxorubicin-sensitive and -resistant MCF-7 cells

| Compound | MCF-7 (Breast) (Dox sensitive) | MCF-7 (Breast) (Dox resistant) | Resistant Factor |
|---|---|---|---|
| doxorubicin | 463 ng/mL | 10000 ng/mL | 21.6× |
| pomiferin | 35.9 μM | 15.2 μM | 0.42× |

TABLE 5

IC$_{50}$ of taxol and pomiferin in taxol-sensitive and -resistant MCF-7 cells

| Compound | MCF-7 (Breast) (Taxol sensitive) | MCF-7 (Breast) (Taxol resistant) | Resistant Factor |
|---|---|---|---|
| Taxol | <1 nM | 5 μM | 5000× |
| Pomiferin | 35.7 μM | 27.1 μM | 0.76× |

TABLE 6

IC$_{50}$ of taxol and pomiferin in taxol-sensitive and -resistant A549 cells

| Compound | A549 (Lung) (Taxol sensitive) | A549 (Lung) (Taxol resistant) | Resistant Factor |
|---|---|---|---|
| Taxol | 30.9 nM | 31.3 μM | 1012.945× |
| Pomiferin | 18.2 μM | 17.2 μM | 0.95× |

TABLE 7

IC$_{50}$ of taxol and pomiferin in taxol-sensitive and -resistant HCT-8 cells

| Compound | HCT-8 (Colon) (Taxol sensitive) | HCT-8 (Colon) (Taxol resistant) | Resistant Factor |
|---|---|---|---|
| Taxol | <1 nM | 35.3 μM | >35300× |
| Pomiferin | 25.5 μM | 17.6 μM | 0.69× |

Example 7

Effects of Pomiferin on Taxol-Mediated Cytotoxicity in Multidrug-Resistant Cancer Cells Cell death and viability are measured using an Annexin V staining kit (BD Biosciences, San Jose, Calif., USA). Multidrug-resistant cancer cells, e.g. A549/HCT-8 taxol-resistant cancer cells were treated with 1-10 μM pomiferin with or without 40 μM of taxol for 24 h. Cells were then harvested and analysed by multiparametric flow cytometry using FITC-Annexin V and propidium iodide staining (BD Biosciences, San Jose, Calif., USA) according to the manufacturer's instructions. Flow cytometry has been then carried out using a FACSCalibur flow cytometer (BD Biosciences, San Jose, Calif., USA). Data acquisition and analysis has been performed with CellQuest (BD Biosciences, San Jose, Calif., USA). Data were obtained from three independent experiments.

In other words, to further address whether the inhibition of P-glycoprotein by pomiferin could sensitize the multidrug-resistant cancer cells to chemotherapeutic compounds, the taxol-resistant cancer cells from lung cancer, A549 and colon cancer, HCT-8 were treated with pomiferin with or without taxol. As shown in FIG. 9A to FIG. 9K, treatment with pomiferin significantly enhanced the taxol-mediated cytotoxicity in these drug-resistant cancer cells. Concomitantly, other taxol-resistant cancer cells from colon (HCT-8) similarly revealed the enhanced taxol-mediated cytotoxicity upon pomiferin treatment (FIG. 10A to FIG. 10K). Collectively, these findings provide further evidence that pomiferin is a potent P-glycoprotein inhibitor able to reverse the drug-resistant phenotype of taxol-resistant cancer cells.

Example 8

Effects of Pomiferin and Further Prenylated Isoflavones in A549 Taxol-Resistant Lung Cancer Cells A Rho123 efflux assay has been carried out. A549 taxol-resistant lung cancer cells were seeded in 6 well-plates at a final concentration of 2×10$^5$ cells per well and cultured for 24 h at 37° C. in an atmosphere containing 5% $CO_2$. At confluence, 3 mL fresh media with 10 μM of pomiferin, pomiferin 3',4'-dimethyl ether, pomiferin trimethyl ether, isopomiferin, osajin, osajin 4'-methyl ether and isoosajin or 10 μM verapamil (known P-glycoprotein inhibitor) was added and incubated further at 37° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 μL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

As shown in FIG. 11A to FIG. 11J, Rho123 dye staining in taxol-resistant lung cancer cells only yielded less than 20% of cell population with fluorescence signal, suggesting that P-glycoprotein in lung origins of taxol-resistant cancer cells effectively pumped out the Rho123 dye from the cells. Addition of the P-glycoprotein inhibitor verapamil significantly suppressed the P-glycoprotein activity, leading to markedly increase of Rho123 fluorescence signal in cells. Consistently, pomiferin dose-dependently inhibited the P-glycoprotein activity, thereby increased the Rho123 accumulation in these taxol-resistant cancer cells. When compared with further prenylated isoflavones, all these compounds including pomiferin 3',4'-dimethyl ether, pomiferin trimethyl ether, isopomiferin, osajin, osajin 4'-methyl ether and isoosajin showed P-glycoprotein inhibition with a different extent, leading to increased levels of Rho123 accumulation in cancer cells. Apparently, isopomiferin and isoosajin proved to have a comparable effect compared to pomiferin on P-glycoprotein inhibition. Collectively, these results demonstrated that the prenylated isoflavones of the present invention have exceptional inhibitory effects on P-glycoprotein.

The invention claimed is:

1. A method for treating a subject suffering from a multidrug-resistant cancer, wherein the cancer is resistant against at least one of taxol or doxorubicin and selected from a multidrug-resistant lung cancer, multidrug-resistant breast cancer, or multidrug-resistant colon cancer, comprising the step of administering an effective amount of a prenylated isoflavone or a pharmaceutically tolerable salt, solvate or anhydrate thereof to the subject, wherein the prenylated isoflavone is based on the general structure of Formula (I):

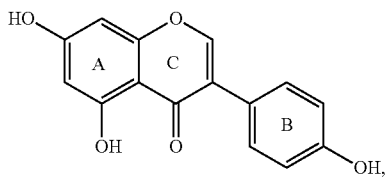

Formula (I)

wherein compared to the general structure of Formula (I) the prenylated isoflavone:
(i) contains at least one prenyl-group attached to a carbon atom in ring A of the general structure of Formula (I); and
(ii) is optionally further modified by at least one of hydroxylation, alkylation, esterification, glycosylation, glucuronidation or hydrogenation.

2. The method of claim 1, wherein the subject is a human and the multidrug-resistant cancer is a multidrug-resistant ABC-protein-dependent cancer.

3. The method of claim 1, wherein the subject is a human and the multidrug-resistant cancer is a multidrug-resistant P-glycoprotein-dependent cancer.

4. The method of claim 1, wherein the prenylated isoflavone has a structure of Formula (II):

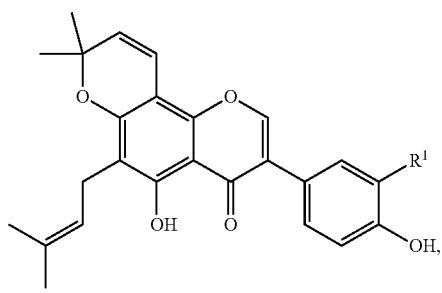

Formula (II)

with $R^1$ being hydrogen or —OH.

5. The method of claim 1, wherein the prenylated isoflavone has the structure of Formula (III):

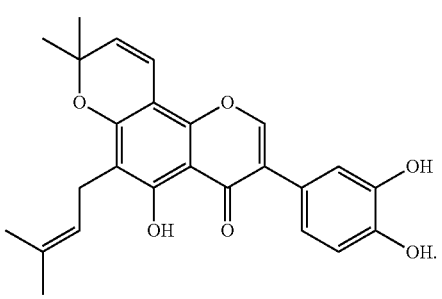

Formula (III)

6. The method of claim 1, wherein the prenylated isoflavone is administered in combination with an effective amount of at least one chemotherapeutic compound which is a substrate for P-glycoprotein, which chemotherapeutic compound is a compound selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog.

7. The method of claim 6, wherein the prenylated isoflavone has a structure of Formula (III):

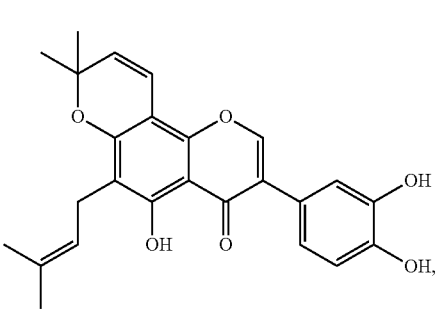

Formula (III)

and wherein the chemotherapeutic compound is selected from taxol or doxorubicin.

8. The method of claim 6, wherein the chemotherapeutic compound is administered before, after or simultaneously with the prenylated isoflavone.

9. A method for specifically targeting cancer cells with multidrug-resistance, wherein the cancer cells are resistant against at least one of taxol or doxorubicin and selected from multidrug-resistant lung cancer cells, multidrug-resistant breast cancer cells, or multidrug-resistant colon cancer cells, comprising the step of contacting a population of cancer cells with multidrug-resistance with a prenylated isoflavone or a salt, solvate or anhydrate thereof, wherein the prenylated isoflavone is based on the general structure of Formula (I):

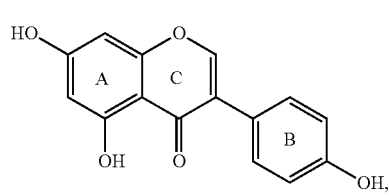

Formula (I)

and wherein compared to the general structure of Formula (I) the prenylated isoflavone:
(i) contains at least one prenyl-group attached to a carbon atom in ring A of the general structure of Formula (I); and
(ii) is optionally further modified by at least one of hydroxylation, alkylation, esterification, glycosylation, glucuronidation or hydrogenation.

10. The method of claim 9, wherein the multidrug-resistant cancer cells are multidrug-resistant P-glycoprotein-dependent cancer cells and wherein the prenylated isoflavone inhibits P-glycoprotein.

11. The method of claim 9, wherein the growth of the multidrug-resistant cancer cells is suppressed or cell death of the multidrug-resistant cancer cells is induced.

12. The method of claim 9, wherein the prenylated isoflavone has a structure of Formula (III):

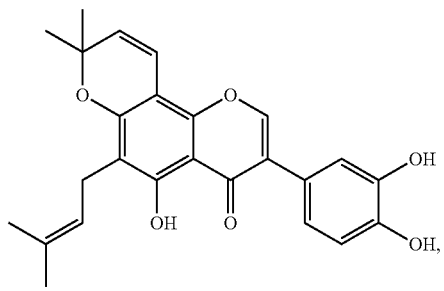

Formula (III)

and wherein the cancer cells are contacted with between 5 µM and 30 µM of said prenylated isoflavone.

13. A method of potentiating the activity of a chemotherapeutic compound in multidrug-resistant cancer cells comprising contacting the multidrug-resistant cancer cells with
(i) a prenylated isoflavone; and
(ii) a chemotherapeutic compound, which chemotherapeutic compound is selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog; and
wherein the multidrug-resistant cancer cells are resistant against at least one of taxol or doxorubicin, wherein the multidrug resistant cancer cells are selected from multidrug-resistant lung cancer cells, multidrug-resistant breast cancer cells, or multidrug-resistant colon cancer cells, and wherein the prenylated isoflavone is based on the general structure of Formula (I):

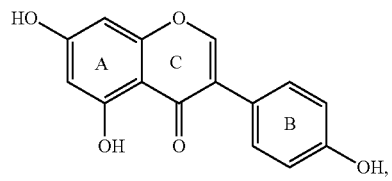

Formula (I)

wherein compared to the general structure of Formula (I) the prenylated isoflavone:
(i) contains at least one prenyl-group attached to a carbon atom in ring A of the general structure of Formula (I); and
(ii) is optionally further modified by at least one of hydroxylation, alkylation, esterification, glycosylation, glucuronidation or hydrogenation.

14. The method of claim 13, wherein the multidrug-resistant cancer cells are contacted with the chemotherapeutic compound before, at the same time or subsequent to the application of the prenylated isoflavone.

15. The method of claim 13, wherein the chemotherapeutic compound is taxol or doxorubicin.

16. The method of claim 13, wherein the activity of the chemotherapeutic compound to inhibit proliferation or inducing cell death of the multidrug-resistant cancer cells is increased.

17. The method of claim 13, wherein the prenylated isoflavone has the structure of Formula (III):

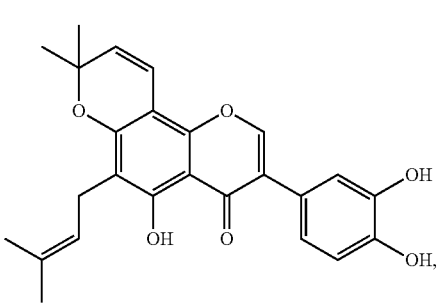

Formula (III)

and the cells are contacted with between 4 µM and 20 µM of the prenylated isoflavone.

* * * * *